United States Patent [19]

Gottschlich et al.

[11] 4,162,314
[45] Jul. 24, 1979

[54] 7[2(SUBSTITUTED PHENYL)2-(AMINO)ACETAMIDO]CEPHALOSPORIN DERIVATIVES

[75] Inventors: Rudolf Gottschlich; Rolf Gericke; Horst Juraszyk; Jürgen Seubert; Wighard Strehlow; Helmut Wahlig; Rolf Bergmann; Elvira Dingeldein, all of Darmstadt, Fed. Rep. of Germany

[73] Assignee: Merck Patent Gesellschaft mit beschrankter Haftung, Darmstadt, Fed. Rep. of Germany

[21] Appl. No.: 806,241

[22] Filed: Jun. 13, 1977

[30] Foreign Application Priority Data

Jun. 14, 1976 [DE] Fed. Rep. of Germany ....... 2626558
Mar. 19, 1977 [DE] Fed. Rep. of Germany ....... 2712225

[51] Int. Cl.² .................. A61K 31/545; C07D 501/22; C07D 501/32
[52] U.S. Cl. .................. 424/246; 544/19; 544/26; 544/30; 260/239.1; 424/271
[58] Field of Search .................. 544/19, 26, 30; 424/246

[56] References Cited

U.S. PATENT DOCUMENTS 3,985,741  10/1976  Crast, Jr. et al. ................ 260/243 C
4,012,382  3/1977  Bouzard et al. ................ 260/243 C Primary Examiner—Donald G. Daus
Assistant Examiner—David E. Wheeler
Attorney, Agent, or Firm—Millen & White

[57] ABSTRACT

Novel β-lactam antibiotics are compounds of the formula:

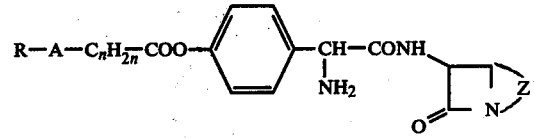

wherein R is alkyl of up to 6 carbon atoms or, when A is oxygen, R is hydrogen; A is oxygen or —OCO—; Z is

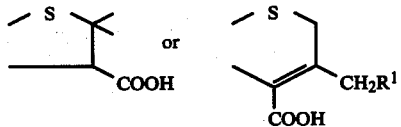

R¹ is hydrogen, acetoxy or S-Het; Het is 1,2,3-triazol-5-yl, 1-methyltetrazol-5-yl, 1,3,4-thiadiazol-2-yl or 2-methyl-1,3,4-thiadiazol-5-yl; and n is an integer from 0 to 8; or a readily-cleavable ester or physiologically-acceptable salt thereof.

5 Claims, No Drawings

7-[2-(SUBSTITUTED PHENYL)-2-(AMINO)ACETAMIDO]CEPHALOSPORIN DERIVATIVES

BACKGROUND OF THE INVENTION

This invention relates to new β-lactam antibiotics and the preparation thereof.

Cephalosporin compounds or cephem-4-carboxylic acid compounds are known and disclosed, e.g., by Flynn, U.S. Pat. No. 3,218,318; Takano et al., U.S. Pat. No. 3,365,449; Holdrege, U.S. Pat. No. 3,687,949; Holdrege, U.S. Pat. No. 3,833,570 and Bickel et al., U.S. Pat. No. 3,929,779, the disclosures of which are incorporated herein by reference.

Penicillin compounds are known and disclosed, e.g., by Erickson, U.S. Pat. No. 3,720,664; Hamanaka, U.S. Pat. No. 3,870,709; Murakami et al., U.S. Pat. No. 3,939,150; Fenes et al., U.S. Pat. No. 3,935,189; Yamada et al., U.S. Pat. No. 3,945,995; Tobiki et al., U.S. Pat. No. 3,951,955; Tobiki et al., U.S. Pat. No. 3,954,733; and Gottschlich et al., Ser. No. 624,763, filed Oct. 22, 1975, now allowed, the disclosures of which are herein incorporated by reference.

SUMMARY OF THE INVENTION

In a compositional aspect, this invention relates to novel compounds of Formula I,

wherein A is

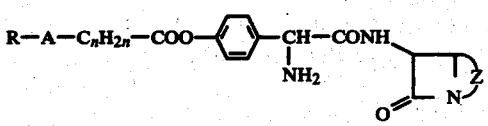

R is alkyl of up to 6 carbon atoms or, when A is —O—, also H; Z is

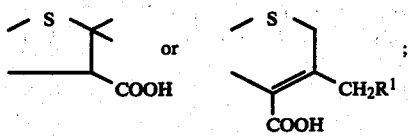

$R^1$ is hydrogen, acetoxy or S-Het; Het is a 1,2,3-triazol-5-yl, 1-methyltetrazol-5-yl, 1,3,4-thiadiazol-2-yl or 2-methyl-1,3,4-thiadiazol-5-yl; and n is an integer from 0 to 8, or a readily-cleavable ester or a physiologically-acceptable salt thereof.

In another compositional aspect, this invention relates to a pharmaceutical composition, comprising an amount per unit dosage effective to produce a systemic antibacterial effect upon administration, of a compound of Formula I, in admixture with a pharmaceutically-acceptable carrier.

In a method-of-use aspect, this invention relates to a method of treating a patient afflicted with a bacterial infection comprising administering to the affected patient an antibacterial amount of a compound of Formula I.

In a preparative aspect, this invention relates to a method for preparing a compound of Formula I, comprising (a) reacting a compound of Formula II

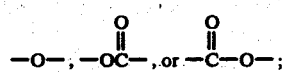

wherein Z is as above, or a functional derivative thereof, with a compound of Formula III

wherein R, A and n are as above, or with a functional derivative or an acid-addition salt thereof; or (b) in a compound which otherwise corresponds to Formula (I) but in which an NH₂ group is present in functionally-modified form or a readily-cleavable ester or physiologically-acceptable salt thereof, liberating the NH₂ group by treatment with a hydrolytic or hydrogenolytic agent; and/or (c) in a thus-obtained compound of Formula (I) or in a readily-cleavable ester or physiologically-acceptable salt thereof, changing a substituent Z by reaction with a reducing or hydrogenolytic agent or by reaction with a thiol HS-Het into a different substituent Z; and/or (d) reacting a compound which otherwise corresponds to Formula (I) but in which R is hydrogen and A is —OC(=O)— or a readily-cleavable ester or a physiologically-acceptable salt thereof with an alkylating agent; and/or (e) converting a compound of Formula (I), by reaction with an esterifying agent, to a readily-cleavable ester; and/or (f) liberating a compound of Formula (I) from a readily-cleavable ester thereof by reaction with a hydrolyzing agent; and/or (g) converting a compound of Formula (I), by reaction with an acid or a base, to a physiologically-acceptable salt thereof and/or (h) liberating a compound of Formula (I) from a salt thereof by reaction with a base or an acid.

DETAILED DESCRIPTION

R is preferably a hydrogen atom, when A is an oxygen atom, or an alkyl of up to 6 carbon atoms, most preferably alkyl of up to 4 carbon atoms, most preferably unbranched alkyl of up to 4 carbon atoms, for example, methyl, ethyl, n-propyl, or n-butyl. R can also be branched alkyl of 3–6, preferably, 3 or 4, carbon atoms, for example, isopropyl, isobutyl, sec.-butyl or tert.-butyl.

Other exemplary R include n-pentyl, 1-methylbutyl, 2-methylbutyl, 3-methylbutyl, 2,2-dimethylpropyl, 1-ethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethyl-1-methylpropyl, 1-ethyl-2-methylpropyl, 1,1,2-trimethylpropyl and 1,2,2-trimethylpropyl.

$R^1$ is preferably acetoxy or S-Het, most preferably acetoxy. When $R^1$ is S-Het, 1-methyl-1,2,3,4-tetrazole-5-mercapto and 1,3,4-thiadiazole-2-mercapto are preferred. $R^1$ can also be 1,2,3-triazole-5-mercapto or 2-methyl-1,3,4-thiadiazole-5-mercapto or hydrogen.

A can be oxygen, carboxy, or oxycarbonyl, the oxygen atom of the oxy group preferably being connected to R, i.e., A can be

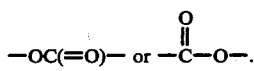

n is 0 or a whole number from 1 to 8, but is preferably 0, especially when A is an oxygen atom, or 1, 2, 3, 4 or 5. n is preferably 2, 3 or 4 when A is $-OC(=O)-$. Thus, $-C_nH_{2n}-$ is preferably a simple bond or methylene, dimethylene, trimethylene, tetramethylene or pentamethylene, but can also be hexamethylene, heptamethylene or octamethylene. However, $-C_nH_{2n}-$ can also be alkylidene or branched alkylene, for example, ethylidene, propylidene, butylidene, pentylidene, propylene, ethylethylene, propylethylene and butylethylene.

Readily-cleavable esters of compounds of Formula (I) include, but are not limited to, tert.-butyl esters, as well as trimethylsilyl, benzyl, benzhydryl, trichloroethyl, benzylmethyl, p-methoxybenzyl, methoxymethyl and pivaloyloxymethyl esters.

Compounds of Formula (I) are preferred in which at least one of R, $R^1$, A and n has one of the above preferred meanings, especially one of those noted as being especially preferred.

Compounds of Formula I therefore include those wherein:

I(a): Z is 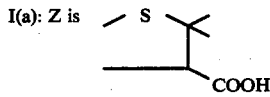

I(b): Z is 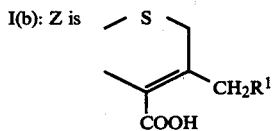

I(c): A is $-O-$, including each of I(a)–I(b);
I(d): A is $-OC(=O)-$ or $-C(=O)-O-$, including each of I(a)–I(b);
I(e): n is 0, including each of I(a)–I(d);
I(f): n is 1, 2, 3, 4, 5, 6, 7 or 8, including each of I(a)–I(d);
I(g): Z is as in I(b) and $R^1$ is S-Het;
I(h): Z is as in I(b) and $R^1$ is acetoxy;
I(i): Z is as in I(b) and $R^1$ is 1-methyltetrazole-5-mercapto;
I(i'): Z is as in I(b) and $R^1$ is 1,3,4-thiadiazole-2-mercapto;
I(j): Z is as in I(a) and A is $-O-$;
I(k): Z is as in I(a) and A is $-OC(=O)-$;
I(l): Z is as in I(a) and n is 0;
I(m): Z is as in I(a) and n is 1,2,3,4 or 5;
I(n): Z is as in I(a), A is $-O-$ and n is 0;
I(o): Z is as in I(a), A is $-OC(=O)-$ and n is 2 or 4;
I(p): Z is as in I(a), A is $-O-$, n is 0 and R is unbranched alkyl of up to 6 carbon atoms;
I(q): Z is as in I(a), A is $-O-$, n is 0 and R is unbranched alkyl of up to 4 carbon atoms;
I(r): Z is as in I(a), A is $-OC(=O)-$, n is 2 or 4 and R is unbranched alkyl of up to 6 carbon atoms;
I(s): Z is as in I(a), A is $-OC(=O)-$, n is 2 or 4 and R is unbranched alkyl of up to 4 carbon atoms;
I(t): Z is as in I(b) and A is $-O-$;
I(u): Z is as in I(b) and A is $-OC(=O)-$;
I(v): Z is as in I(b), A is $-O-$, n is 0 and R is unbranched alkyl of up to 4 carbon atoms;
I(w): Z is as in I(b), A is $-O-$, n is 0, R is unbranched alkyl of up to 4 carbon atoms and $R^1$ is acetoxy or S-Het;
I(x): Z is as in I(b), A is $-OC(=O)-$, n is 2 or 4 and R is unbranched alkyl of up to 4 carbon atoms;
I(y): Z is as in I(b), A is $-OC(=O)-$, n is 2 or 4, R is unbranched alkyl of up to 4 carbon atoms and $R^1$ is acetoxy or S-Het;
I(z): A is oxygen and R is hydrogen, including each of I(a), I(b), I(e) and I(f);
I(aa): R is alkyl of 1–6 carbon atoms, including each of I(a)–I(f);
I(bb): $R^1$ is hydrogen, including each of I(a)–I(f) and I(z)–I(aa);
I(cc): $R^1$ is acetoxy, including each of I(a)–I(f), I(z) and I(aa);
I(dd): $R^1$ is S-Het, including each of I(a)–I(f), I(z) and I(aa);
I(ee): Het is 1,2,3-triazolyl, including each of I(a)–I(f), I(z) and I(aa);
I(ff): Het is 1-methyltetrazolyl, including each of I(a)–I(f), I(z) and I(aa);
I(hh): Het is 2-methyl-1,3,4-thiadiazol-2-yl, including each of I(a)–I(f), I(z) and I(aa); and
I(ii): n is 1, 2, 3, 4 or 5, including each of I(a)–I(d) and I(z)–I(hh).

The α-carbon atom of the substituted phenylacetyl radical which forms the side chain in compounds of Formula (I) is asymmetrical. Therefore, the present invention includes pure epimers in which this carbon atom has the D-configuration and those pure epimers in which this carbon atom has the L-configuration, as well as epimeric mixtures of compounds of Formula (I), in which some of the α-carbon atoms of the side chains are of the D- and some of the L-configuration. Of the Epimer mixtures those are preferred in which the D- and the L-configuration occur in substantially equal amounts. Compounds of Formula (I) and especially of Formulae I(a) to I(ii) are particularly preferred in which the carbon atom of the side chain is of the D-configuration.

The compounds of Formula (I) are prepared according to methods which are known in cephalosporin and penicillin chemistry and which are described in more detail in the literature, for example "Advances in Penicillin Research" in Advances in Drug Research, Vol. 7, p. 1 (1973), "The Cephalosporin Group of Antibiotics" in Advances in Pharmacology and Chemotherapy, Vol. 13, p. 83 (1975), and "Cephalosporins" in Advances in Drug Research Vol. 4, p. 1 (1967) and the literature cited.

The present invention also provides mixtures which contain adjuvant and/or carrier materials customary in pharmacy, together with at least one compound of Formula (I) and/or at least one physiologically-acceptable salt and/or at least one readily-cleavable ester thereof.

This invention also relates to the use of a compound of Formula (I) or a physiologically-acceptable salt or of a readily-cleavable ester thereof for the preparation of pharmaceutical compositions, especially by physical methods.

The present invention also provides a process for the preparation of pharmaceutical compositions, wherein at least one compound of Formula (I) and/or at least one physiologically-acceptable salt thereof and/or at least one readily-cleavable ester thereof, optionally together with at least one solid, liquid or semi-liquid adjuvant and/or carrier material and optionally together with at least one additional active material, is converted to an appropriate dosage form.

Some of the starting materials for the process of the present invention are known and some are new. The new compounds can be prepared by known methods, analogously to those used for the known compounds. For example, cephem derivatives of Formula (II) ($R^1 = -S$-Het) can be obtained from 7-aminocephalosporanic acid (7-ACA; II, $R^1 = -OCOCH_3$) by reaction with known heterocyclic thiols of the formula Het—SH, or with related metal mercaptides, for example, by reaction of the corresponding alkali metal salts in hot aqueous acetone.

As functional derivatives of acids of Formula (II), can be used readily-cleavable esters, for example, tert.-butyl esters or trimethylsilyl esters, which can be formed in situ from (II) and N-trimethylsilylacetamide, and the other easily-splittable esters given above. The salts, especially neutral salts, of these acids can be used. For example, the alkali metal, e.g., sodium or potassium; alkaline earth metal, e.g., magnesium or calcium; and ammonium salts, can be used. Of the latter, it is preferred to use salts derived from amines, especially from tert.-amines, for example, triethylamine, triethanolamine, pyridine and collidine. The salts can be used in the reaction as such or can be produced in situ from an acid of Formula (II) and a base, for example, sodium bicarbonate, disodium hydrogen phosphate or triethylamine.

Acids of Formula (III) are derived from 2-(p-hydroxyphenyl)-glycine. They are obtained from this known compound, after blocking the amino group with one of the protective groups usual in peptide chemistry, by reaction with an acid of Formula (IV)

$$R-A-C_nH_{2n}-COOH \quad\quad (IV)$$

wherein R, A and n are as above, or with an activated derivative of this acid.

Activated derivatives of acids of Formula (IV) are preferably the halides, most preferably chlorides and bromides; anhydrides and mixed anhydrides, azides and activated esters. For example, esters include those from p-nitrophenol, 2,4-dinitrophenol, p-nitrophenylmercaptan, methylene cyanohydrin or N-hydroxysuccinimide. As mixed anhydrides of acids of Formula (IV) can be used, for example, those of the lower alkanoic acids, especially of acetic acid or substituted acetic acids, e.g., trichloroacetic acid, pivalic acid and cyanoacetic acid. Anhydrides with carbonic acid hemiesters, which can be obtained by reaction of an acid of Formula (IV) with benzyl, p-nitrobenzyl, isobutyl, ethyl or allyl chloroformate, can also be used. These functional derivatives of (IV) are preferably produced in situ and further reacted without isolation.

Compounds of Formula (IV) are known. They are preferably ω-alkoxycarboxylic acids of 3–15 carbon atoms, more preferably, 3–8 carbon atoms, the alkoxy of which are preferably unbranched and contain up to 4 carbon atoms. For example, preferred compounds include, but are not limited to, 2-methoxyacetic acid, 2-ethoxyacetic acid, 4-methoxybutyric acid, 4-butyloxybutyric acid, 8-ethoxycaprylic acid and 9-ethoxypelargonic acid. Other compounds of Formula (IV) include α,ω-dicarboxylic acid monoalkyl esters of 3–14 carbon atoms, preferably 5–9 carbon atoms, preferably of unbranched alkyl esters of up to 4 carbon atoms, such as monoethyl malonate, monoethyl and monobutyl succinate and monoethyl and monobutyl adipate. Derivatives of branched dicarboxylic acids, such as monoethyl methylmalonate and monomethyl 2-ethylsuccinate, can also be used.

A third important group of compounds of Formula (IV) are carbonic acid hemiesters of 2 to 7 carbon atoms, preferably of 2 to 5 carbon atoms, which are preferably in the form of acid chlorides, i.e., alkyl chloroformates. Typical examples of alkyl chloroformates include methyl, ethyl, butyl, hexyl and tert.-butyl chloroformates.

In general, the reaction of 2-(p-hydroxyphenyl)glycine, wherein the amino group is present in protected form, for example, as a tert.-butyloxycarbonylamino or 2-ethoxycarbonyl-1-methylvinylamino, with a compound of Formula (IV), or with an activated derivative thereof, takes place in an inert solvent. Especially preferred solvents include, but are not limited to, chlorinated hydrocarbons, for example, methylene chloride or chloroform; ethers, for example, diethyl ether, tetrahydrofuran (THF) or dioxane; ketones, for example, acetone or butanone; amides, for example, dimethyl formamide (DMF), dimethyl acetamide or phosphoric acid hexamethyl triamide (HMPT); sulfoxides, for example, dimethyl sulfoxide (DMSO); water; and organic or aqueous inorganic bases. Mixtures of these solvents can also be used.

The reaction temperature can be from about −70° to about +80° C., preferably from −50° to +30° C., most preferably from −40° to +10° C. The reaction time depends on the nature of the starting materials used and on the reaction temperature. Normally, it is from 5 minutes to 72 hours.

When a compound of Formula (II) or a functional derivative thereof is reacted with an activated derivative of Formula (III), the activated derivative is always present as acid-addition salt, the proton thereof serving as an amino-blocking group and preventing self-acylation. The term "functional derivative" means not only a compound in which a functional group is present in protected form in such a manner that this group cannot interfere in a particular reaction, but also a compound in which a particular functional group is present in activated form in order to react especially well in the desired reaction. Of course, both functional changes can be present simultaneously, for example, in the reactions of interest here, an amino acid can be used as an activated acid derivative and the amino group can be simultaneously blocked by a protective group.

Preferred acid-addition salts of compounds of Formula (III) are those with strong acids, especially with strong mineral acids, such as hydrochloric, hydrobromic, hydriodic, sulfuric and nitric acids, and possibly also with strong organic acids, for example, trichloracetic or trifluoroacetic acid.

It is especially preferred to use for acylation of a compound of Formula (II) or of a functional derivative thereof, a hydrochloride of the acid chloride of a compound of Formula (III).

Reaction of a compound of Formula (II) or of a functional derivative with a compound of Formula (III) or with a functional derivative takes place, as a rule, in an inert solvent under reaction conditions corresponding to those given above for the acylation of 2-(p-hydroxyphenyl)-glycine. The reaction temperature is preferably between −40° and +10° C. The period of reaction depends on the nature of the starting materials selected and the reaction temperature and is usually from about 10 minutes to 80 hours.

Examples of solvents which can be used include the solvents mentioned above for the acylation of 2-(p-hydroxyphenyl)-glycine with a compound of Formula (V) or with an activated derivative thereof.

Acylation of the 7-amino group of a cephalosporin, for example, of 7-aminocephalosporanic acid (7-ACA), or of the 6-amino group of a penicillin (6-APA), is a known reaction and any functional equivalent of a compound of Formula (III) which is usually employed as an acylating agent for primary amino groups can be used. Examples of appropriate acylating derivatives (activated derivatives) of the free acid are known. The free acid can be coupled with a compound of Formula (II) or with one of its readily-cleavable esters, for example, in the presence of an enzyme or of an N,N'-carbonyldiimidazole or of an N,N'-carbonylditriazole or of a carbodiimide reggent, for example, N,N'-diisopropyl carbodiimide, N,N'-dicyclohexyl carbodiimide or N-cyclohexyl-N'-(2-morpholinoethyl)-carbodiimide.

Other useable activated derivatives include the corresponding azolides, i.e., amides of corresponding acids, the amide nitrogen of which is a member of a quasiaromatic 5-membered ring which contains at least two nitrogen atoms, for example, of an imidazole, pyrazole, triazole, benzimidazole or benzotriazole ring. Another useable derivative of a substituted phenylglycine of Formula (III) is a N-carboxyanhydride (Leuchs' anhydride). The group which activates the carboxyl group here also protects the amino group.

It is especially preferred to react a readily-cleavable ester, preferably a tert.-butyl ester, of an acid of Formula (II) with a compound of Formula (III) in which the amino group is present in protected form (a water-binding agent advantageously being added) and subsequently hydrolyzing or hydrogenolyzing to liberate the amino group in the reaction product obtained. As water-accepting agents can be used, for example, carbodiimides, and especially dicyclohexyl carbodiimide (DCC).

For example, 7-ACA tert.-butyl ester or 6-APA tert.-butyl ester can be reacted with a compound of Formula (V)

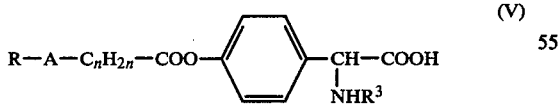

(V)

wherein $R_3$ is a protecting group which can be split off and R, A and n are as above, with a hydrolytic or hydrogenolytic agent and with DCC in substantially equimolar proportions, with cooling, in an inert solvent, especially in a chlorinated hydrocarbon, such as methylene chloride; in an ether, such as THF; or in an aprotic dipolar solvent, such as DMF or DMSO; or in a solvent mixture.

Reaction of a compound of Formula (II) or of a functional derivative thereof with an activated derivative, or a salt thereof, of an acid of Formula (III) is preferably carried out in the presence of a basic catalyst. Examples of basic catalysts which can be used include inorganic metal hydroxides, preferably alkali metal or alkaline earth metal hydroxides and basic salts, as well as organic amines, preferably tertiary organic amines. It is especially preferable to use sodium bicarbonate, sodium carbonate, potassium carbonate, sodium hydroxide, potassium hydroxide, pyridine or a base of low nucleophilicity, for example, a tertiary amine, such as triethylamine, N-methylmorpholine or ethyldiisopropylamine; or pottasium tert.-butylate.

$R_3$ is a protective group which is readily removed by hydrolysis or hydrogenolysis, particularly those known from peptide chemistry. Exemplary protective groups, are arylmethoxycarbonyl radicals, such as benzyloxycarbonyl; and alkyloxycarbonyl radicals, such as tert.-butyloxy-carbonyl (BOC); arylsulfonyl radicals, such as p-bromophenylsulfonyl or p-tolylsulfonyl; arylmethyl radicals such as benzyl, diphenylmethyl or triphenylmethyl; acyl radicals, preferably alkanoyl, such as formyl, acetyl or pivaloyl, or substituted alkanoyl, such as trifluoroacetyl, chloroacetyl or o-nitrophenoxyacetyl; aryloxycarbonyl radicals, such as phenoxycarbonyl; alkylthiocarbonyl or aralkylthiocarbonyl radicals such as benzylthiocarbonyl; or activated vinyl radicals, such as 2-ethoxycarbonyl-1-methylvinyl.

The β-lactam compounds of Formula (I) can also be obtained from compounds containing a functionally-modified $NH_2$ group but which otherwise correspond to Formula (I) by liberating the $NH_2$ group in known manner.

Starting materials for these process variants can be obtained, for example, by reacting a compound of Formula (II) with a compound of Formula (V). It is especially advantageous to react a compound of Formula (II) or a functional derivative thereof with a compound of Formula (VI):

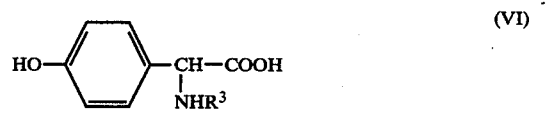

(VI)

wherein $R^3$ is as above, or with a functional derivative thereof, and to further react the thus-produced compound of Formula (VII)

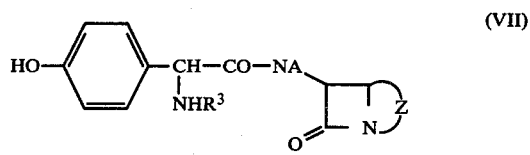

(VII)

wherein Z and $R^3$ are as above, or a functional derivative or salt thereof, with a compound of Formula (IV) or with an activated derivative thereof.

Conditions for the reaction of a compound of Formula (VII) or of a functional derivative or salt thereof with a compound of Formula (IV) or with an activated derivative thereof correspond to conditions already described for the reaction of a compound of Formula (II) or a functional derivative thereof with a compond of Formula (III) or a functional derivative thereof.

A functionally-modified amino group can be liberated by methods described in the literature, especially by hydrolysis or by hydrogenolysis. Solvolysis, preferably hydrolysis, especially of a tert.-butyloxycarbonylamino group, can be carried out, for example, with trifluoroacetic acid or with an aqueous mineral acid, such as hydrochloric acid, at a temperature from −10° to 50° C. Hydrogenolysis, especially the removal of benzyl, tert.-butoxycarbonyl or carbobenzyloxy radicals, can be carried out by hydrogenation in the presence of a noble metal catalyst, e.g., 5 to 50% palladium-on-charcoal or palladium oxide. Hydrogenolysis is preferably carried out a temperature from −10° to 50° C., especially at ambient temperature, at a pressure of 1 to 10 ats., preferably at atmospheric pressure. Especially mild hydrogenation conditions must be selected in order to avoid undesired reduction, for example, of the C=C double bond of the cephem system.

Compounds of Formula (VII) or functional derivatives or salts thereof can be reacted with an acid of Formula (IV), in which A can be a

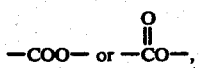

i.e., R is bonded to the carbon atom of the carbonyl group, or with an activated derivative of these acids to give, after removal of the protective group ($R^3$), the desired compounds of Formula (I). Conditions for this reaction have already been described.

A compound which otherwise corresponds to Formula (I) but in which R is hydrogen and A is —OC(=O)— or a readily-cleavable ester or physiologically-compatible salt thereof can be converted by reaction with an alkylating agent to a compound of Formula (I). Preferred alkylating agents include alkanols of up to 6 carbon atoms, such as methanol, ethanol, n-propanol, n-butanol, isopropanol, sec.-butanol, isobutanol, tert.-butanol, pentanol, pentan-2-ol, hexanol and hexan-2-ol; and acid esters, particularly alkane carboxylic acid esters, for example, formates, acetates, propionates and pivalates of the above alcohols. Alkyl halides derived from the above alcohols can also be used as alkylating agents, especially alkyl bromides of up to 6 carbon atoms.

Reaction of a compound which otherwise corresponds to Formula (I), but in which R is hydrogen and A is a —OC(=O)— group, with an alkylating agent usually takes place in the presence of an acidic catalyst, preferably of a mineral acid, such as hydrochloric, hydrobromic or sulfuric acid, or of an organic acid, especially of a sulfonic acid, such as p-toluene-sulfonic acid.

It is advantageous to carry out the alkylation in the presence of a water-accepting agent, such as DCC, or to remove the water fromed by azetropic distillation when the alkylating agent used is an alcohol of up to 4 carbon atoms. It is usual to work in inert solvents, for example, hydrocarbons, such as benzene, or chlorinated hydrocarbons, such as dichloromethan, chloroform, carbon tetrachloride or 1,2-dichloroethane, using an excess of alkylating agent. It is also possible to use the alkylating agent as solvent.

When the alkylating agent used is an alkyl halide of up to 6 carbon atoms, the carboxyl group H—OC(=O)— (A=—OC(=O)—, R=H) is preferably in the form of a salt, preferably the silver salt. The alkylation temperature is preferably from 0° to 100° C.

Other alkylating agents which can be used include diazoalkanes of up to 6 carbon atoms, preferably diazomethane. Alkylation with these compounds is preferably carried out in an ether, such as diethyl ether or dioxane, preferably at a temperature of from 0° to 40° C., most preferably ambient temperature.

The hydrolyzing agent with which a compound of Formula (I) can be liberated from a readily-cleavable ester thereof is preferably water in the presence of a base, especially an inorganic base, such as an alkali metal hydroxide or carbonate, for example, sodium hydroxide, potassium hydroxide, sodium carbonate or potassium carbonate; or of an organic base, such as triethylamine, triethanolamine or piperidine. Inert organic solvents can also be present. A mixture of dioxane, acetone or dimethyl formamide and water is preferred as reaction medium. As a rule, the hydrolysis temperature is from 10° to 80° C., preferably ambient temperature.

If desired, a residue $R^1$ can be exchanged for another residue $R^1$ in a thus-obtained product of Formula (I) or in an easily-splittable ester or physiologically-compatible salt thereof.

It is especially advantageous to convert a cephalosporanic acid of Formula (I) ($R^1$=OCOCH$_3$), by reaction with a mercaptan of the formula Het—SH, to the corresponding thioether ($R^1$=SHet). A salt of a cephalosporanic acid of Formula (I) is preferably reacted with a salt of the thiol in aqueous acetone at temperatures from 20° to 100° C. and at a pH from 4 to 8. The alkali metal salts, particularly the sodium salt, can be used. This synthesis route is especially preferred for the preparation of compounds of Formula (I) in which A is oxygen and n is not equal to 0.

As already explained, compounds of Formula (I) have a center of asymmetry in the side chain attached to the β-lactam ring. Therefore, they are usually obtained in the form of mixtures of two epimeric forms which, because of their differing physical properties, can be isolated from the mixture and obtained in pure form, for example, by recrystallization from appropriate solvents or by chromatographic methods, including adsorption chromatographic and partition chromatographic methods and mixed forms thereof. Instead of the compounds themselves, readily crystallizable derivatives thereof, can be used.

It is possible to obtain pure diastereomeric compounds of Formula (I) by the above-described methods by using, for example, as starting materials compounds of Formula (III) or activated derivatives thereof which are already optically active.

Optically active compounds of Formula (III) or activated derivatives thereof can be prepared from the racemates by known methods, described in the literature. For the resolution of racemic α-amino acids, chemical methods are preferred.

Accordingly, diastereomers are formed from the racemic mixture by reaction with an optically-active adjuvant. An optically-active base can be reacted with the carboxyl group of a compound of Formula (III). For example, diastereomeric salts of compounds of Formula (III) can be formed with optically-active amines, such as quinine, brucine, morphine or 1-phenylethylamine.

The amino group can also be used to form appropriate diastereomeric salts by reaction with an optically-active acid, for example (+)- and (−)-tartaric acid, camphoric acid or β-camphorsulfonic acid. An ester of the amino acid is preferably used.

The difference in the solubilities of the particular diastereomeric salts obtained permits selective crystallization of one form and regeneration of the particular optically-active compounds from the mixture.

A free carboxylic acid of Formula (I) can also be converted into a readily-cleavable carboxylic acid ester by esterification. For example, tert.-butyl esters can be obtained by reaction of the acids with isobutylene.

Acid (I) can be liberated from an ester, for example, by solvolysis, especially by acid hydrolysis. The tert.-butyl esters especially advantageously obtained in the synthesis can be split, for example, with trifluoroacetic acid at a temperature from 0° to 40° C.

The compounds of the present invention are solid crystalline or amorphous products. They form solid, frequently crystalline alkali metal, ammonium and alkaline earth metal salts, as well as salts with organic bases, such as diethylamine, triethylamine, diethanolamine, N-ethyldiethanolamine, pyrrolidine, piperidine, N-ethylpiperidine, 1-(2-hydroxyethyl)-piperidine, morpholine, procaine, benzylamine, dibenzylamine and 1-phenyl-2-propylamine and other amines usually employed for the preparation of cephalosporin salts.

Of the alkali metal salts, sodium and potassium salts are of special importance. They can be prepared by mixing a solution of an acid of Formula (I) in an organic solvent with a solution of a sodium or potassium salt of a fatty acid, for example, of diethylacetic or 2-ethylcapronic acid, in a solvent, for example, acetone or n-butanol, or in a solvent mixture. The salts which thereby precipitate out directly or upon the addition of diethyl ether, can be filtered off.

Basic compounds of Formula (I) can be converted with acids in the usual way to the related acid-addition salts, for example, to the hydrochlorides or citrates.

Compound of Formula (I) do not possess sharp melting points, and are preferably characterized by other physical characteristics, especially advantageously by nuclear resonance spectra. They can also be characterized by thin layer chromatograms, preferably using Merck DC-finished plates silica gel $F_{254}$ (elution agent, e.g., dioxane/water 85:15 v/v).

Compounds of Formula I have excellent anti-bacterial activity against gram-negative and gram-positive microorganisms, especially in vivo. In comparison with known semi-synthetic cephalosporins and penicillins, the new compounds exhibit marked differences with regard to sensitivity of individual microorganisms. In numerous cases, the new compounds are considerably better than known β-lactam antibiotics so that, for combatting particular bacterial infections, they possess decisive therapeutic advantages. New compounds of Formula (I), when administered orally, exhibit outstanding anti-bacterial activity, for example in mice, against Staphylococcus aureus (measured as DC 50).

The new compounds can be employed as pharmaceuticals, especially for combatting bacterial infections and can be used as intermediates for the preparation of other pharmaceuticals.

The new compounds can be used in admixture with solid, liquid and/or semi-liquid adjuvant and/or carrier materials usual in pharmacy, for example, for pharmaceuticals in human and veterinary medicine.

The adjuvant and/or carrier materials used include organic or inorganic materials which can be employed for enteral, preferably oral, or, for parenteral or topical administration and which do not react with the new compounds, e.g., water, vegetable oils, benzyl alcohol, polyethylene glycols, gelatine, lactose, starch, magnesium stearate, talc, petroleum jelly or cholesterol.

For enteral use, for example, tablets, capsules, dragees, syrups, juices, granulates (dry juices) or suppositories, can be used. For parenteral administration, solutions, preferably oily or aqueous solutions, suspensions, emulsions or implants, can be used, and for topical use, salves, creams, lotions, pastes or powders.

The adjuvant and/or carrier materials customary in pharmacy, especially those recited above, can be mixed with one or more compounds of Formula (I) and/or readily-cleavable esters and/or physiologically-compatible salts thereof to obtain appropriate compositions for the desired mode of administration.

These compositions can be sterilized or mixed with adjuvant materials, emulsifiers, salts for influencing osmotic pressure, buffer substances and/or coloring materials.

Compounds of Formula (I), as well as the readily-cleavable esters and physiologically-acceptable salts thereof can be used essentially in the same way as the known compound cephalexin for combatting infections. They are preferably administered in dosages of 1 to 5000, especially of 200 to 2000, mg. per dosage unit. The daily dosage is preferably from 4 to 100, most preferably, 10 to 60 mg. per kg. of body weight.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

Each of the compounds of Formula (I) in the following Examples can be used for the preparation of pharmaceutical compositions.

IR spectra were measured in KBr.

$R_f$ values for penicillanic compounds were measured on silica gel using dioxane-water (85:15 v/v) as eluant and for cephem compounds on silica gel with dioxane-water (9:1 v/v) as eluant.

NMR spectra were recorded in dimethyl sulfoxide.

The following abbreviations are used in the Examples: DMF=dimethylformamide, 7-ACA=7-aminocephalosporanic acid, 6-APA=6-aminopenicillanic acid, DCC=dicyclohexyl carbodiimide, THF=tetrahydrofuran, BOC=tert.-butyloxycarbonyl, EMV=2-ethoxycarbonyl-1-methylvinyl, MCC=3-methyl-3-cephem-4-carboxylic acid, CC=-3-cephem-4-carboxylic acid, CA=-cephalosporanic acid, PA=-penicillanic acid.

Insofar as not otherwise stated, substituted 2-phenylglycines of Formula (II), or the derivatives thereof, are used in the form of racemates. The corresponding compounds of Formula (I) are then obtained as mixtures of two epimers.

EXAMPLE 1

The triethylammonium salt of 6-[D-2-(EMV-amino)-2-p-hydroxyphenylacetamido]-PA (4.33 g.), prepared by gentle warming of equimolar amounts of 6-(D-2-amino-p-hydroxyphenylacetamido)-PA (amoxycillin) and ethyl acetoacetate in dichloromethane in the presence of triethylamine is dissolved in 50 ml. of dichloromethane and 2.1 ml. of triethylamine and cooled with ice, while 1.45 ml. of ethyl chloroformate dissolved in 5 ml. of dichloromethane are added dropwise thereto. The reaction mixture is stirred and cooled with ice for 30 minutes more. Solvent is distilled off and the oily residue is taken up in 50 ml. of THF and extracted with 100 ml. of dilute aqueous sodium bicarbonate solution. The aqueous phase, after washing with diethyl ether, is adjusted to pH 3 and extracted with ethyl acetate. The organic phase is allowed to stand overnight and thus-formed 6-(2-D-amino-p-ethoxycarbonyloxyphenylacetamido)-PA formed is precipitated by the addition of petroleum ether: $R_f=0.41$ (silica gel/dioxane:water=85:15 v/v); IR: 1690, 1760 and 1770 cm.$^{-1}$ (shoulder).

As in Example 1, reaction of the triethylammonium salt of 6-[2-D-(EMV-amino)-2-p-hydroxyphenylacetamido]-PA, with the corresponding alkyl chloroformates, i.e., acid chlorides of carbonic acid hemiesters of Formula (IV) (A=—O—, n=0), and subsequent removal of the amino-blocking group during the work up gives penicillanic acid derivatives of Formula (I):

| Example | Penicillanic Acid Derivative of Formula (I) |
|---|---|
| 2. | 6-(2-D-amino-2-p-methoxycarbonyloxyphenyl-acetamido)-PA |
| 3. | 6-(2-D-amino-2-p-propyloxycarbonyloxyphenyl-acetamido)-PA |
| 4. | 6-(2-D-amino-2-p-isopropyloxycarbonyloxyphenylacetamido)-PA |
| 5. | 6-(2-D-amino-2-p-butyloxycarbonyloxyphenyl-acetamido)-PA, $R_f=0.44$, IR = 1765, 1670 cm.$^{-1}$ |
| 6. | 6-(2-D-amino-2-p-isobutyloxycarbonyloxyphenyl-acetamido)-PA |
| 7. | 6-(2-D-amino-2-p-sec.-butyloxycarbonyloxyphenylacetamido)-PA |
| 8. | 6-(2-D-amino-2-p-tert.-butyloxycarbonyloxyphenylacetamido)-PA |
| 9. | 6-(2-D-amino-2-p-pentyloxycarbonyloxyphenyl-acetamido)-PA |
| 10. | 6-(2-D-amino-2-p-isopentyloxycarbonyloxy-phenylacetamido)-PA |
| 11. | 6-(2-D-amino-2-p-hexyloxycarbonyloxyphenyl-acetamido)-PA, $R_f = 0.45$ |
| 12. | 6-(2-D-amino-2-p-isohexyloxycarbonyloxyphenyl-acetamido)-PA |

EXAMPLE 13

The triethylammonium salt of 7-[2-D-(EMV-amido-2-p-hydroxyphenylacetamido]-CA (6.34 g.), prepared by warming equimolar amounts of 7-(2-D-amino-2-p-hydroxyphenylacetamido)-CA and ethyl acetoacetate in dichloromethane in the presence of triethylamine, is dissolved in 60 ml. of dichloromethane and 2.3 ml. of triethylamine and cooled with ice while 1.25 g. of ethyl chloroformate, dissolved in 8 ml. of dichloromethane, are added dropwise thereto. The reaction mixture is cooled with ice and stirred for 45 minutes and worked up as described in Example 1 to give 7-(2-D-amino-2-p-ethoxycarbonyloxyphenylacetamido)-CA.

Analogously to Example 13, the triethylammonium salt of 7-[2-D-(EMV-amido)-2-p-hydroxyphenylacetamido]-CA, is reacted with a corresponding alkyl chloroformate of Formula (IV). Subsequent removal of the amino-blocking group during the work up gives the following cephalosporanic acids of Formula (I):

| Example | Cephalosporanic Acid Derivative of Formula (I) |
|---|---|
| 14. | 7-(2-D-amino-2-p-methoxycarbonyloxyphenyl-acetamido)-CA |
| 15. | 7-(2-D-amino-2-propyloxycarbonyloxyphenyl-acetamido)-CA, $R_f = 0.35$ |
| 16. | 7-(2-D-amino-2-p-isopropyloxycarbonyloxyphenyl-acetamido)-CA, $R_f = 0.29$ |
| 17. | 7-(2-D-amino-2-p-butyloxycarbonyloxyphenyl-acetamido)-CA |
| 18. | 7-(2-D-amino-2-p-isobutyloxycarbonyloxyphenyl-acetamido)-CA |
| 19. | 7-(2-D-amino-2-p-sec.-butyloxycarbonyloxyphenyl-acetamido)-CA |
| 20. | 7-(2-D-amino-2-p-tert.-butyloxycarbonyloxy-phenylacetamido)-CA |
| 21. | 7-(2-D-amino-2-p-pentyloxycarbonyloxyphenyl-acetamido)-CA |
| 22. | 7-(2-D-amino-2-isopentyloxycarbonyloxyphenyl-acetamido)-CA |
| 23. | 7-(2-D-amino-2-p-hexyloxycarbonyloxyphenyl-acetamido)-CA, $[\alpha]_D^{20} = +43.6°$ (in ethanol), $R_f = 0.36$ |
| 24. | 7-(2-D-amino-2-p-isohexyloxycarbonyloxyphenyl-acetamido)-CA |

As in Example 13, the triethylammonium salt of 7-[2-D-(EMV-amino)-2-p-hydroxyphenylacetamido]-MCC is reacted with a corresponding alkyl chloroformate of Formula (IV). Removal during the work up of the amino-blocking group produces the following 3-methyl-3-cephem-4-carboxylic acid derivatives of Formula (I):

| Example | 3-Methyl-3-cephem-4-carboxylic Acid Derivative of Formula (I) |
|---|---|
| 25. | 7-(2-D-amino-2-p-methoxycarbonyloxyphenyl-acetamido-MCC |
| 26. | 7-(2-D-amino-2-p-ethoxycarbonyloxyphenyl-acetamido)-MCC |
| 27. | 7-(2-D-amino-2-p-propyloxycarbonyloxyphenyl-acetamido)-MCC |
| 28. | 7-(2-D-amino-p-isopropyloxycarbonyloxyphenyl-acetamido)-MCC |
| 29. | 7-(2-D-amino-2-p-butyloxycarbonyloxyphenyl-acetamido)-MCC |
| 30. | 7-(2-D-amino-2-p-isobutyloxycarbonyloxyphenyl-acetamido)-MCC |
| 31. | 7-(2-D-amino-2-p-sec.-butyloxycarbonyloxyphenyl-acetamido)-MCC |
| 32. | 7-(2-D-amino-2-p-tert.-butyloxycarbonyloxy-phenylacetamido)-MCC |
| 33. | 7-(2-D-amino-2-p-pentyloxycarbonyloxyphenyl-acetamido)-MCC |
| 34. | 7-(2-D-amino-2-p-isopentyloxycarbonyloxyphenyl-acetamido)-MCC |
| 35. | 7-(2-D-amino-2-p-hexyloxycarbonyloxyphenyl-acetamido)-MCC |
| 36. | 7-(2-D-amino-2-p-isohexyloxycarbonyloxyphenyl-acetamido)-MCC |

By the process of Example 13, the triethylammonium salt of 7-[2-D-(EMV-amino)-2-p-hydroxyphenylacetamido]-3-(1,2,3-triazolyl-5-mercaptomethyl)-CC, is reacted with an alkyl chloroformate of Formula (IV). Subsequent removal during the work up of the amino protective group yields the following 3-(1,2,3-triazolyl-5-mercaptomethyl-3-cephem-4-carboxylic acid derivatives of Formula (I):

| Example | 3-(1,2,3-Triazolyl-5-mercaptomethyl)-3-cephem-4-carboxylic Acid Derivative of Formula (I) |
|---|---|
| 37. | 7-(2-D-amino-2-p-methoxycarbonyloxyphenyl-acetamido)-3-(1,2,3-triazolyl-5-mercapto- |

| Example | 3-(1,2,3-Triazolyl-5-mercaptomethyl)-3-cephem-4-carboxylic Acid Derivative of Formula (I) |
|---|---|
| | methyl)-CC |
| 38. | 7-(2-D-amino-2-p-ethoxycarbonyloxyphenylacetamido)-3-(1,2,3-triazolyl-5-mercaptomethyl)-CC |
| 39. | 7-(2-D-amino-2-p-propyloxycarbonyloxyphenylacetamido)-3-(1,2,3-triazolyl-5-mercaptomethyl)-CC |
| 40. | 7-(2-D-amino-2-p-isopropyloxycarbonyloxyphenylacetamido)-3-(1,2,3-triazolyl-5-mercaptomethyl)-CC |
| 41. | 7-(2-D-amino-2-p-butyloxycarbonyloxyphenylacetamido)-3-(1,2,3-triazolyl-5-mercaptomethyl)-CC |
| 42. | 7-(2-D-amino-2-p-isobutyloxycarbonyloxyphenylacetamido)-3-(1,2,3-triazolyl-5-mercaptomethyl)-CC |
| 43. | 7-(2-D-amino-2-p-sec.-butyloxycarbonyloxyphenylacetamido)-3-(1,2,3-triazolyl-5-mercaptomethyl)-CC |
| 44. | 7-(2-D-amino-2-p-tert.-butyloxycarbonyloxyphenylacetamido)-3-(1,2,3-triazolyl-5-mercaptomethyl)-CC |
| 45. | 7-(2-D-amino-2-p-pentyloxycarbonyloxyphenylacetamido)-3-(1,2,3-triazolyl-5-mercaptomethyl)-CC |
| 46. | 7-(2-D-amino-2-p-isopentyloxycarbonyloxyphenylacetamido)-3-(1,2,3-triazolyl-5-mercaptomethyl)-CC |
| 47. | 7-(2-D-amino-2-p-hexyloxycarbonyloxyphenylacetamido)-3-(1,2,3-triazolyl-5-mercaptomethyl)-CC |
| 48. | 7-(2-D-amino-2-p-isohexyloxycarbonyloxyphenylacetamido)-3-(1,2,3-triazolyl-5-mercaptomethyl)-CC |

As in Example 13, the triethylammonium salt of 7-[2-D-(EMV-amino)-2-p-hydroxyphenylacetamido]-3-(1-methyltetrazolyl-5-mercaptomethyl)-CC is converted, by reaction with an alkyl chloroformate of Formula (IV) and subsequent cleavage of the amino protective group during the work up to the following 3-(1-methyltetrazolyl-5-mercaptomethyl)-3-cephem-4-carboxylic acid derivatives of Formula (I):

| Example | 3-(1-Methyltetrazolyl-5-mercaptomethyl)-3-cephem-4-carboxylic Acid Derivatives of Formula (I) |
|---|---|
| 49. | 7-(2-D-amino-2-p-methoxycarbonyloxyphenylacetamido)-3-(1-methyltetrazolyl-5-mercaptomethyl)-CC |
| 50. | 7-(2-D-amino-2-p-ethoxycarbonyloxyphenylacetamido)-3-(1-methyltetrazolyl-5-mercaptomethyl)-CC |
| 51. | 7-(2-D-amino-2-p-propyloxycarbonyloxyphenylacetamido)-3-(1-methyltetrazolyl-5-mercaptomethyl)-CC |
| 52. | 7-(2-D-amino-2-p-isopropyloxycarbonyloxyphenylacetamido)-3-(1-methyltetrazolyl-5-mercaptomethyl)-CC |
| 53. | 7-(2-D-amino-2-p-butyloxycarbonyloxyphenylacetamido)-3-(1-methyltetrazolyl-5-mercaptomethyl)-CC |
| 54. | 7-(2-D-amino-2-p-isobutyloxycarbonyloxyphenylacetamido)-3-(1-methyltetrazolyl-5-mercaptomethyl)-CC |
| 55. | 7-(2-D-amino-2-p-sec.-butyloxycarbonyloxyphenylacetamido)-3-(1-methyltetrazolyl-5-mercaptomethyl)-CC |
| 56. | 7-(2-D-amino-2-p-tert.-butyloxycarbonyloxyphenylacetamido)-3-(1-methyltetrazolyl-5-mercaptomethyl)-CC |
| 57. | 7-(2-D-amino-2-p-pentyloxycarbonyloxyphenylacetamido)-3-(1-methyltetrazolyl-5-mercaptomethyl)-CC |
| 58. | 7-(2-D-amino-2-p-isopentyloxycarbonyloxyphenylacetamido)-3-(1-methyltetrazolyl-5-mercaptomethyl)-CC |
| 59. | 7-(2-D-amino-2-p-hexyloxycarbonyloxyphenyl- |

| Example | 3-(1-Methyltetrazolyl-5-mercaptomethyl)-3-cephem-4-carboxylic Acid Derivatives of Formula (I) |
|---|---|
| | acetamido)-3-(1-methyltetrazolyl-5-mercaptomethyl)-CC |
| 60. | 7-(2-D-amino-2-p-isohexyloxycarbonyloxyphenylacetamido)-3-(1-methyltetrazolyl-5-mercaptomethyl)-CC |

By the method of Example 13, the triethylammonium salt of 7-[2-D-(EMV-amino)-2-p-hydroxyphenylacetamido]-3-(1,3,4-thiadiazolyl-2-mercaptomethyl)-CC reacts with corresponding alkyl chloroformates of Formula (IV). Subsequent work up results in cleavage of the amino protective group. 3-(1,3,4-Thiadiazolyl-2-mercaptomethyl)-3-cephem-4-carboxylic acid derivatives of Formula (I) are obtained:

| Example | 3-(1,3,4-Thiadiazolyl-2-mercaptomethyl)-3-cephem-4-carboxylic Acid Derivatives of Formula (I) |
|---|---|
| 61. | 7-(2-D-amino-2-p-methoxycarbonyloxyphenylacetamido)-3-(1,3,4-thiadiazolyl-2-mercaptomethyl)-CC |
| 62. | 7-(2-D-amino-2-p-ethoxycarbonyloxyphenylacetamido)-3-(1,3,4-thiadiazolyl-2-mercaptomethyl)-CC |
| 63. | 7-(2-D-amino-2-p-propyloxycarbonyloxyphenylacetamido)-3-(1,3,4-thiadiazolyl-2-mercaptomethyl-CC |
| 64. | 7-(2-D-amino-2-p-isopropyloxycarbonyloxyphenylacetamido)-3-(1,3,4-thiadiazolyl-2-mercaptomethyl)-CC |
| 65. | 7-(2-D-amino-2-p-butyloxycarbonyloxyphenylacetamido)-3-(1,3,4-thiadiazolyl-2-mercaptomethyl)-CC |
| 66. | 7-(2-D-amino-2-p-isobutyloxycarbonyloxyphenylacetamido)-3-(1,3,4-thiadiazolyl-2-mercaptomethyl)-CC |
| 67. | 7-(2-D-amino-2-p-sec.-butyloxycarbonyloxyphenylacetamido)-3-(1,3,4-thiadiazolyl-2-mercaptomethyl)-CC |
| 68. | 7-(2-D-amino-2-p-tert.-butyloxycarbonyloxyphenylacetamido)-3-(1,3,4-thiadiazolyl-2-mercaptomethyl)-CC |
| 69. | 7-(2-D-amino-2-p-pentyloxycarbonyloxyphenylacetamido)-3-(1,3,4-thiadiazolyl-2-mercaptomethyl)-CC |
| 70. | 7-(2-D-amino-2-p-isopentyloxycarbonyloxyphenylacetamido)-3-(1,3,4-thiadiazolyl-2-mercaptomethyl)-CC |
| 71. | 7-(2-D-amino-2-p-hexyloxycarbonyloxyphenylacetamido)-3-(1,3,4-thiadiazolyl-2-mercaptomethyl)-CC |
| 72. | 7-(2-D-amino-2-p-isohexyloxycarbonyloxyphenylacetamido)-3-(1,3,4-thiadiazolyl-2-mercaptomethyl)-CC |

As in Example 13, the triethylammonium salt of 7-[2-D-(EMV-amino)-2-p-hydroxyphenylacetamido]-3-(2-methyl-1,3,4-thiadiazolyl-5-mercaptomethyl)-CC reacts with corresponding alkyl chloroformates of Formula (IV). Subsequent removal of the amino protective group during the work up produces the following 3-(2-methyl-1,3,4-thiadiazolyl-5-mercaptomethyl)-3-cephem-4-carboxylic acid derivatives of Formula (I):

| Ex. | 3-(2-Methyl-1,3,4-thiadiazolyl-5-mercaptomethyl)-3-cephem-4-carboxylic Acid Derivatives of Formula (I) |
|---|---|
| 73. | 7-(2-D-amino-2-p-methoxycarbonyloxyphenylacetamido)-3-(2-methyl-1,3,4-thiadiazolyl-5-mercaptomethyl)-CC |
| 74. | 7-(2-D-amino-2-p-ethoxycarbonyloxyphenylacetamido)-3-(2-methyl-1,3,4-thiadiazolyl-5-mercaptomethyl)-CC |
| 75. | 7-(2-D-amino-2-p-propyloxycarbonyloxyphenylacetamido)-3-(2-methyl-1,3,4-thiadiazolyl-5-mercapto- |

| Ex. | 3-(2-Methyl-1,3,4-thiadiazolyl-5-mercaptomethyl)-3-cephem-4-carboxylic Acid Derivatives of Formula (I) |
|---|---|
| | methyl-CC |
| 76. | 7-(2-D-amino-2-p-isopropyloxycarbonyloxyphenyl-acetamido)-3-(2-methyl-1,3,4-thiadiazolyl-5-mercaptomethyl)-CC |
| 77. | 7-(2-D-amino-2-p-butyloxycarbonyloxyphenylacet-amido)-3-(2-methyl-1,3,4-thiadiazolyl-5-mercaptomethyl)-CC |
| 78. | 7-(2-D-amino-2-p-isobutyloxycarbonyloxyphenyl-acetamido)-3-(2-methyl-1,3,4-thiadiazolyl-5-mercaptomethyl)-CC |
| 79. | 7-(2-D-amino-2-p-sec.-butyloxycarbonyloxyphenyl-acetamido)-3-(2-methyl-1,3,4-thiadiazolyl-5-mercaptomethyl)-CC |
| 80. | 7-(2-D-amino-2-p-tert.-butyloxycarbonyloxyphenyl-acetamido)-3-(2-methyl-1,3,4-thiadiazolyl-5-mercaptomethyl)-CC |
| 81. | 7-(2-D-amino-2-p-pentyloxycarbonyloxyphenyl-acetamido)-3-(2-methyl-1,3,4-thiadiazolyl-5-mercaptomethyl)-CC |
| 82. | 7-(2-D-amino-2-p-isopentyloxycarbonyloxyphenyl-acetamido)-3-(2-methyl-1-3,4,-thiadiazolyl-5-mercaptomethyl)-CC |
| 83. | 7-(2-D-amino-2-p-hexyloxycarbonyloxyphenyl-acetamido)-3-(2-methyl-1,3,4-thiadiazolyl-5-mercaptomethyl)-CC |
| 84. | 7-(2-D-amino-2-p-isohexyloxycarbonyloxyphenyl-acetamido)-3-(2-methyl-1,3,4-thiadiazolyl-5-mercaptomethyl)-CC |

EXAMPLE 85

The triethylammonium salt of 6-(2-D-EMV-amino-2-p-hydroxyphenylacetamido)-penicillanic acid (2.89 g.), prepared by warming equimolar amounts of 6-(2-amino-2-p-hydroxyphenylacetamido)-penicillanic acid and ethyl acetoacetate in dichloromethane in the presence of triethylamine, is dissolved in 250 ml. of dichloromethane and 5.6 ml. of triethylamine and cooled with ice while 1.87 g. of adipic acid monomethyl ester chloride dissolved in 40 ml. of dichloromethane are added dropwise thereto. Stirring and cooling with ice is continued for 30 minutes more. The solvent is distilled off and the oily residue is dissolved in 50 ml. of THF and filtered. The filtrate is added, with stirring, to 250 ml. of dilute aqueous sodium bicarbonate solution. The organic solvent is distilled off and the aqueous solution is extracted with ethyl acetate. The aqueous phase is adjusted to pH 3 with 1 N hydrochloric acid and extracted with 200 ml. of ethyl acetate. After standing overnight, precipitation is carried out with petroleum ether to give 6-[2-D-amino-2-p-methoxycarbonylpentanoyloxy)-phenylacetamido]-penicillanic acid; $R_f$=0.43 (silica gel/dioxane: water=85:15); IR: 1685, 1735, 1760 and 1770 cm.$^{-1}$ (shoulder).

As in Example 85, the triethylammonium salt of 6-(2-D-EMV-amino-2-p-hydroxyphenylacetamido)-PA reacts with acid chlorides of monoalkyl esters of dicarboxylic acids of Formula (IV)

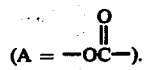

Subsequent removal of the amino protective group during the work up gives the following penicillanic acid derivatives of Formula (I):

| Example | Penicillanic Acid Derivative of Formula (I) |
|---|---|
| 86. | 6-[2-D-amino-2-p-(5-ethoxycarbonylpentanoyloxy-phenylacetamido]-PA |
| 87. | 6-[2-D-amino-2-p-(5-propyloxycarbonylpentanoyl-oxy)-phenylacetamido]-PA |
| 88. | 6-[2-D-amino-2-p-(5-butyloxycarbonylpentanoyl-oxy)-phenylacetamido]-PA |
| 89. | 6-[2-D-amino-2-p-(5-pentyloxycarbonylpentanoyl-oxy)-phenylacetamido]-PA |
| 90. | 6-[2-D-amino-2-p-(5-hexyloxycarbonylpentanoyl-oxy)-phenylacetamido]-PA |
| 91. | 6-[2-D-amino-2-p-(2-methoxycarbonylacetoxy)-phenylacetamido]-PA |
| 92. | 6-[2-D-amino-2-p-(3-methoxycarbonylpropanoyl-oxy)-phenylacetamido]-PA, $R_f$ = 0.36, IR: 1763, 1735, 1680 cm.$^{-1}$ |
| 93. | 6-[2-D-amino-2-p-(4-methoxycarbonylbutanoyloxy)-phenylacetamido]-PA |
| 94. | 6-[2-D-amino-2-p-(6-methoxycarbonylhexanoyloxy)-phenylacetamido]-PA, $R_f$ = 0.40, IR: 1770 (shoulder), 1760 and 1735 cm.$^{-1}$ |
| 95. | 6-[2-D-amino-2-p-(7-methoxycarbonylheptanoyl-oxy)-phenylacetamido]-PA |
| 96. | 6-[2-D-amino-2-p-(8-methoxycarbonyloctanoyl-oxy)-phenylacetamido]-PA |
| 97. | 6-[2-D-amino-2-p-(9-methoxycarbonylnonanoyloxy)-phenylacetamido]-PA |
| 98. | 6-[2-D-amino-2-p-(2-ethoxycarbonylacetoxy)-phenylacetamido]-PA |
| 99. | 6-[2-D-amino-2-p-(2-butoxycarbonylacetoxy)-phenylacetamido]-PA |
| 100. | 6-[2-D-amino-2-p-(2-hexyloxycarbonylacetoxy)-phenylacetamido]-PA |
| 101. | 6-[2-D-amino-2-p-(3-ethoxycarbonylpropanoyloxy)-phenylacetamido]-PA |
| 102. | 6-[2-D-amino-2-p-(4-ethoxycarbonylbutanoyloxy)-phenylacetamido]-PA |
| 103. | 6-[2-D-amino-2-p-(7-ethoxycarbonylheptanoyloxy-phenylacetamido]-PA |
| 104. | 6-[2-D-amino-2-p-(9-ethoxycarbonylnonanoyloxy)-phenylacetamido]-PA |
| 105. | 6-[2-D-amino-2-p-(3-butyloxycarbonylpropanoyl-oxy)-phenylacetamido]-PA |
| 106. | 6-[2-D-amino-2-p-(3-hexyloxycarbonylpropanoyl-oxy)-phenylacetamido] -PA |
| 107. | 6-[2-D-amino-2-p-(4-butyloxycarbonylbutanoyl-oxy)-phenylacetamido]-PA |
| 108. | 6-[2-D-amino-2-p-(4-hexyloxycarbonylbutanoyl-oxy)-phenylacetamido]-PA |
| 109. | 6-[2-D-amino-2-p-(7-butyloxycarbonylheptanoyl-oxy)-phenylacetamido]-PA |
| 110. | 6-[2-D-amino-2-p-(7-hexyloxycarbonylheptanoyl-oxy)-phenylacetamido]-PA |
| 111. | 6-[2-D-amino-2-p-(9-butyloxycarbonylnonanoyl-oxy)-phenylacetamido]-PA |
| 112. | 6-[2-D-amino-2-p-(9-hexyloxycarbonylnonanoyl-oxy)-phenylacetamido]-PA |

By the procedure of Example 85, the triethylammonium salt of 7-[2-D-(EMV-amino)-2-p-hydroxy-phenylacetamido]-CA is reacted with acid chlorides of corresponding alkyl esters of dicarboxylic acids of Formula (IV)

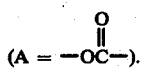

After cleavage of the amino protective group during the work up, the following cephalosporanic acids of Formula (I) are obtained:

| Example | Cephalosporanic Acid of Formula (I) |
|---|---|
| 113. | 7-[2-D-amino-2-p-(5-methoxycarbonylpentanoyl-oxy)-phenylacetamido]-CA; [α]$_D^{20}$ = +49.6° (in ethanol) |

-continued

| Example | Cephalosporanic Acid of Formula (I) |
|---|---|
| 114. | 7-[2-D-amino-2-p-(5-ethoxycarbonylpentanoyloxy)-phenylacetamido]-CA; $[\alpha]_D^{20} = +78.0°$ (in ethanol) |
| 115. | 7-[2-D-amino-2-p-(5-butyloxycarbonylpentanoyloxy)-phenylacetamido]-CA |
| 116. | 7-[2-D-amino-2-p-(5-hexyloxycarbonylpentanoyloxy)-phenylacetamido]-CA |
| 117. | 7-[2-D-amino-2-p-(2-methoxycarbonylacetoxy)-phenylacetamido]-CA |
| 118. | 7-[2-D-amino-2-p-(2-ethoxycarbonylacetoxy)-phenylacetamido]-CA |
| 119. | 7-[2-D-amino-2-p-(2-butyloxycarbonylacetoxy)-phenylacetamido]-CA |
| 120. | 7-[2-D-amino-2-p-(2-hexyloxycarbonylacetoxy)-phenylacetamido]-CA |
| 121. | 7-[2-D-amino-2-p-(3-ethoxycarbonylpropanyloxy)-phenylacetamido]-CA; $[\alpha]_D^{20} = +37.6°$ (in ethanol) |
| 122. | 7-[2-D-amino-2-p-(4-ethoxycarbonylbutanoyloxy)-phenylacetamido]-CA |
| 123. | 7-[2-D-amino-2-p-(6-methoxycarbonylhexanoyloxy)-phenylacetamido]-CA; $[\alpha]_D^{20} = +67.6°$ (in ethanol) |
| 124. | 7-[2-D-amino-2-p-(7-ethoxycarbonylheptanoyloxy)-phenylacetamido]-CA |
| 125. | 7-[2-D-amino-2-p-(9-ethoxycarbonylnonanoyloxy)-phenylacetamido]-CA |

In accordance with Example 85, the triethylammonium salt of 7-[2-D-(EMV-amino)-2-p-hydroxyphenylacetamido]-MCC is reacted with acid chlorides of appropriate monoalkyl esters of dicarboxylic acids of Formula (IV)

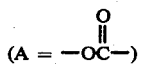

and worked up to remove the amino protective group. 3-Methyl-3-cephem-4-carboxylic acid derivatives of Formula (I) are obtained:

| Example | 3-Methyl-3-cephem-4-carboxylic Acid Derivative of Formula (I) |
|---|---|
| 126. | 7-[2-D-amino-2-p-(5-methoxycarbonylpentanoyloxy)-phenylacetamido]-MCC |
| 127. | 7-[2-D-amino-2-p-(5-ethoxycarbonylpentanoyloxy)-phenylacetamido]-MCC |
| 128. | 7-[2-D-amino-2-p-(5-butyloxycarbonylpentanoyloxy)-phenylacetamido]-MCC |
| 129. | 7-[2-D-amino-2-p-(5-hexyloxycarbonylpentanoyloxy)-phenylacetamido]-MCC |
| 130. | 7-[2-D-amino-2-p-(2-methoxycarbonylacetoxy)-phenylacetamido]-MCC |
| 131. | 7-[2-D-amino-2-p-(2-ethoxycarbonylacetoxy)-phenylacetamido]-MCC |
| 132. | 7-[2-D-amino-2-p-(2-butyloxycarbonylacetoxy)-phenylacetamido]-MCC |
| 133. | 7-[2-D-amino-2-p-(2-hexyloxycarbonylacetoxy)-phenylacetamido]-MCC |
| 134. | 7-[2-D-amino-2-p-(3-methoxycarbonylpropanoyloxy)-phenylacetamido]-MCC, $R_f = 0.58$ |
| 135. | 7-[2-D-amino-2-p-(4-ethoxycarbonylbutanoyloxy)-phenylacetamido]-MCC |
| 136. | 7-[2-D-amino-2-p-(6-ethoxycarbonylhexanoyloxy)-phenylacetamido]-MCC |
| 137. | 7-[2-D-amino-2-p-(7-ethoxycarbonylheptanoyloxy)-phenylacetamido]-MCC |
| 138. | 7-[2-D-amino-2-p-(8-ethoxycarbonylnonanoyloxy)-phenylacetamido]-MCC |

By the procedure of Example 85, the triethylammonium salt of 7-[2-D-(EMV-amino)-2-p-hydroxyphenylacetamido]-3-(1,2,3-triazolyl-5-mercaptomethyl)-CC reacts with the acid chlorides of appropriate monoalkyl esters of dicarboxylic acids of Formula (IV)

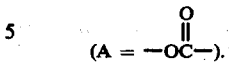

Subsequent splitting off of the amino protective group during the work up provides the following 3-(1,2,3-triazolyl-5-mercaptomethyl)-3-cephem-4-carboxylic acid derivatives of Formula (I):

| Example | 3-(1,2,3-Triazolyl-5-mercaptomethyl)-3-cephem-4-carboxylic Acid Derivatives of Formula (I) |
|---|---|
| 139. | 7-[2-D-amino-2-p-(5-methoxycarbonylpentanoyloxy)-phenylacetamido]-3-(1,2,3-triazolyl-5-mercaptomethyl)-CC |
| 140. | 7-[2-D-amino-2-p-(5-ethoxycarbonylpentanoyloxy)-phenylacetamido]-3-(1,2,3-triazolyl-5-mercaptomethyl)-CC |
| 141. | 7-[2-D-amino-2-p-(5-butyloxycarbonylpentanoyloxy)-phenylacetamido]-3-(1,2,3-triazolyl-5-mercaptomethyl)-CC |
| 142. | 7-[2-D-amino-2-p-(5-hexyloxycarbonylpentanoyloxy)-phenylacetamido]-3-(1,2,3-triazolyl-5-mercaptomethyl)-CC |
| 143. | 7-[2-D-amino-2-p-(2-methoxycarbonylacetoxy)-phenylacetamido]-3-(1,2,3-triazolyl-5-mercaptomethyl)-CC |
| 144. | 7-[2-D-amino-2-p-(2-ethoxycarbonylacetoxy)-phenylacetamido]-3-(1,2,3-triazolyl-5-mercaptomethyl)-CC |
| 145. | 7-[2-D-amino-2-p-(3-ethoxycarbonylpropanoyloxy)-phenylacetamido]-3-(1,2,3-triazolyl-5-mercaptomethyl)-CC |
| 146. | 7-[2-D-amino-2-p-(4-ethoxycarbonylbutanoyloxy)-phenylacetamido]-3-(1,2,3-triazolyl-5-mercaptomethyl)-CC |
| 147. | 7-[2-D-amino-2-p-(6-ethoxycarbonylhexanoyloxy)-phenylacetamido]-3-(1,2,3-triazolyl-5-mercaptomethyl)-CC |
| 148. | 7-[2-D-amino-2-p-(7-ethoxycarbonylheptanoyloxy)-phenylacetamido]-3-(1,2,3-triazolyl-5-mercaptomethyl)-CC |
| 149. | 7-[2-D-amino-2-p-(9-ethoxycarbonylnonanoyloxy)-phenylacetamido]-3-(1,2,3-triazolyl-5-mercaptomethyl)-CC |

Analogously to Example 85, the triethylammonium salt of 7-[2-D-(EMV-amino)-2-p-hydroxyphenylacetamido]-3-(1-methyltetrazolyl-5-mercaptomethyl)-CC and acid chlorides of corresponding monoalkyl esters of dicarboxylic acids of Formula (IV)

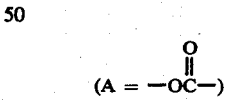

are reacted and the product worked up, with cleavage of the amino protective group, to obtain the following 3-(1-methyltetrazolyl-5-mercaptomethyl)-3-cephem-4-carboxylic acid derivatives of Formula (I):

| Example | 3-(1-Methyltetrazolyl-5-mercaptomethyl)-3-cephem-4-carboxylic Acid Derivative of Formula (I) |
|---|---|
| 150. | 7-[2-D-amino-2-p-(5-methoxycarbonylpentanoyloxy)-phenylacetamido]-3-(1-methyltetrazolyl-5-mercaptomethyl)-CC |
| 151. | 7-[2-D-amino-2-p-(5-ethoxycarbonylpentanoyloxy)-phenylacetamido]-3-(1-methyltetrazolyl-5-mercaptomethyl)-CC |
| 152. | 7-[2-D-amino-2-p-(5-butyloxycarbonylpentanoyl- |

| Example | 3-(1-Methyltetrazolyl-5-mercaptomethyl)-3-cephem-4-carboxylic Acid Derivative of Formula (I) |
|---|---|
| | oxy)-phenylacetamido]-3-(1-methyltetrazolyl-5-mercaptomethyl)-CC |
| 153. | 7-[2-D-amino-2-p-(5-hexyloxycarbonylpentanoyloxy)-phenylacetamido]-3-(1-methyltetrazolyl-5-mercaptomethyl)-CC |
| 154. | 7-[2-D-amino-2-p-(2-methoxycarbonylacetoxy)-phenylacetamido]-3-(1-methyltetrazolyl-5-mercaptomethyl)-CC |
| 155. | 7-[2-D-amino-2-p-(2-ethoxycarbonylacetoxy)-phenylacetamido]-3-(1-methyltetrazolyl-5-mercaptomethyl)-CC |
| 156. | 7-(2-D-amino-2-p-(3-methoxycarbonylpropanoyloxy)-phenylacetamido]-3-(1-methyltetrazolyl-5-mercaptomethyl)-CC; $[\alpha]_D^{20} = +21.8$ (in methanol) |
| 157. | 7-[2-D-amino-2-p-(4-ethoxycarbonylbutanoyloxy)-phenylacetamido]-3-(1-methyltetrazolyl-5-mercaptomethyl)-CC |
| 158. | 7-[2-D-amino-2-p-(6-ethoxycarbonylhexanoyloxy)-phenylacetamido]-3-(1-methyltetrazolyl-5-mercaptomethyl)-CC |
| 159. | 7-[2-D-amino-2-p-(7-ethoxycarbonylheptanoyloxy)-phenylacetamido]-3-(1-methyltetrazolyl-5-mercaptomethyl)-CC |
| 160. | 7-[2-D-amino-2-p-(9-ethoxycarbonylnonanoyloxy)-phenylacetamido]-3-(1-methyltetrazolyl-5-mercaptomethyl)-CC |

Analogously to Example 85, the triethylammonium salt of 7-[2-D-(EMV-amino)-2-p-hydroxyphenylacetamido]-3-(1,3,4-thiadiazolyl-2-mercaptomethyl)-CC and acid chlorides of appropriate monoalkyl esters of dicarboxylic acids of Formula (IV)

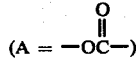

produce, after subsequent work up with removal of the amino protective group, the following 3-(1,3,4-thiadiazolyl-2-mercaptomethyl)-3-cephem-4-carboxylic acid derivatives of Formula (I):

| Example | 3-(1,3,4-Thiadiazolyl-2-mercaptomethyl)-3-cephem-4-carboxylic Acid Derivative of Formula (I) |
|---|---|
| 161. | 7-[2-D-amino-2-p-(5-methoxycarbonylpentanoyloxy)-phenylacetamido]-3-(1,3,4-thiadiazolyl-2-mercaptomethyl)-CC |
| 162. | 7-[2-D-amino-2-p-(5-ethoxycarbonylpentanoyloxy)-phenylacetamido]-3-(1,3,4-thiadiazolyl-2-mercaptomethyl)-CC |
| 163. | 7-[2-D-amino-2-p-(5-butyloxycarbonylpentanoyloxy)-phenylacetamido]-3-(1,3,4-thiadiazolyl-2-mercaptomethyl)-CC |
| 164. | 7-[2-D-amino-2-p-(5-hexyloxycarbonylpentanoyloxy)-phenylacetamido]-3-(1,3,4-thiadiazolyl-2-mercaptomethyl)-CC |
| 165. | 7-[2-D-amino-2-p-(2-methoxycarbonylacetoxy)-phenylacetamido]-3-(1,3,4-thiadiazolyl-2-mercaptomethyl)-CC |
| 166. | 7-[2-D-amino-2-p-(2-ethoxycarbonylacetoxy)-phenylacetamido]-3-(1,3,4-thiadiazolyl-2-mercaptomethyl)-CC |
| 167. | 7-[2-D-amino-2-p-(3-ethoxycarbonylpropanoyloxy)-phenylacetamido]-3-(1,3,4-thiadiazolyl-2-mercaptomethyl)-CC |
| 168. | 7-[2-D-amino-2-p-(4-ethoxycarbonylbutanoyloxy)-phenylacetamido]-3-(1,3,4-thiadiazolyl-2-mercaptomethyl)-CC |
| 169. | 7-[2-D-amino-2-p-(6-ethoxycarbonylhexanoyloxy)-phenylacetamido]-3-(1,3,4-thiadiazolyl-2-mercaptomethyl)-CC |
| 170. | 7-[2-D-amino-2-p-(7-ethoxycarbonylheptanoyloxy)-phenylacetamido]-3-(1,3,4-thiadiazolyl-2-mercaptomethyl)-CC |
| 171. | 7-[2-D-amino-2-p-(9-ethoxycarbonylnonanoyloxy)-phenylacetamido]-3-(1,3,4-thiadiazolyl-2-mercaptomethyl)-CC |

Analogously to Example 85, from the triethylammonium salt of 7-[2-D-(EMV-amino)-2-p-hydroxyphenylacetamido]-3-(1,3,4-thiadiazolyl-5-mercaptomethyl)-CC, by reaction with corresponding alkyl chloroformates of Formula (IV)

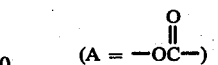

and cleavage of the amino protective group during the work up are obtained the following 3-(2-methyl-1,3,4-thiadiazolyl-5-mercaptomethyl)-3-cephem-4-carboxylic acid derivatives of Formula (I):

| Example | 3-(2-Methyl-1,3,4-thiadiazolyl-5-mercaptomethyl)-3-cephem-4-carboxylic Acid Derivative of Formula (I) |
|---|---|
| 172. | 7-[2-D-amino-2-p-(5-methoxycarbonylpentanoyloxy)-phenylacetamido]-3-(2-methyl-1,3,4-thiadiazolyl-5-mercaptomethyl)-CC |
| 173. | 7-[2-D-amino-2-p-(5-ethoxycarbonylpentanoyloxy)-phenylacetamido]-3-(2-methyl-1,3,4-thiadiazolyl-5-mercaptomethyl)-CC |
| 174. | 7-[2-D-amino-2-p-(5-butyloxycarbonylpentanoyloxy)-phenylacetamido]-3-(2-methyl-1,3,4-thiadiazolyl-5-mercaptomethyl)-CC |
| 175. | 7-[2-D-amino-2-p-(5-hexyloxycarbonylpentanoyloxy)-phenylacetamido]-3-(2-methyl-1,3,4-thiadiazolyl-5-mercaptomethyl)-CC |
| 176. | 7-[2-D-amino-2-p-(2-methoxycarbonylacetoxy)-phenylacetamido]-3-(2-methyl-1,3,4-thiadiazolyl-5-mercaptomethyl)-CC |
| 177. | 7-[2-D-amino-2-p-(2-ethoxycarbonylacetoxy)-phenylacetamido]-3-(2-methyl-1,3,4-thiadiazolyl-5-mercaptomethyl)-CC |
| 178. | 7-[2-D-amino-2-p-(3-ethoxycarbonylpropanoyloxy)-phenylacetamido]-3-(2-methyl-1,3,4-thiadiazolyl-5-mercaptomethyl)-CC |
| 179. | 7-[2-D-amino-2-p-(4-ethoxycarbonylbutanoyloxy)-phenylacetamido]-3-(2-methyl-1,3,4-thiadiazolyl-5-mercaptomethyl)-CC |
| 180. | 7-[2-D-amino-2-p-(6-ethoxycarbonylhexanoyl)-oxy)-phenylacetamido]-3-(2-methyl-1,3,4-thiadiazolyl-5-mercaptomethyl)-CC |
| 181. | 7-[2-D-amino-2-p-(7-ethoxycarbonylheptanoyloxy)-phenylacetamido]-3-(2-methyl-1,3,4-thiadiazolyl-5-mercaptomethyl)-CC |
| 182. | 7-[2-D-amino-2-p-(9-ethoxycarbonylnonanoyloxy)-phenylacetamido]-3-(2-methyl-1,3,4-thiadiazolyl-5-mercaptomethyl)-CC |

EXAMPLE 183

The triethylammonium salt of 6-(2-D-EMV-amino-2-p-hydroxyphenylacetamido)-PA (5.78 g.) is dissolved in 500 ml. of dichloromethane and 1.3 g. of triethylamine and cooled with ice while 2.0 g. of 3-ethoxycarbonyl-2-methylpropanoyl chloride, dissolved in 60 ml. of dichloromethane, are added thereto. Stirring and cooling with ice is continued for 30 minutes more. The solvent is distilled off. The residue is dissolved in THF and filtered. The filtrate is added to 250 ml. dilute aqueous sodium bicarbonate solution. The organic solvent is distilled off and the aqueous phase is washed with ethyl acetate and then the aqueous phase is adjusted with 1 N hydrochloric acid to pH 4.5 and extracted with 300 ml. of ethyl acetate. The solvent is distilled off to give, after chromatographic purification of the residue (silica gel/dioxane:water=85:15 v/v), 6-[2-D-amino-2-p-(3-ethoxycarbonyl-2-methylpropanoyloxy)phenylacetamido]-PA.

Analogously to Example 183, the reaction of triethylammonium salts of 7-(2-D-EMV-amino-2-p-hydroxyphenylacetamido)-cephem derivatives of Formula (VII) with 3-ethoxycarbonyl-2-methylpropanoyl chloride and 2-ethoxycarbonyl-2-ethylethanoyl chloride and subsequent splitting off of the amino protective group during the isolation procedure produces the following compounds of Formula (I):

| Example | Compound of Formula (I) |
|---|---|
| 184. | 7-[2-D-amino-2-p-(3-ethoxycarbonyl-2-methyl-propanoyloxy)-phenylacetamido]-CA |
| 185. | 7-[2-D-amino-2-p-(3-ethoxycarbonyl-2-methyl-propanoyloxy)-phenylacetamido]-MCC |
| 186. | 7-[2-D-amino-2-p-(3-ethoxycarbonyl-2-methyl-propanoyloxy)-phenylacetamido]-3-(1,2,3-triazolyl-5-mercaptomethyl)-CC |
| 187. | 7-[2-D-amino-2-p-(3-ethoxycarbonyl-2-methyl-propanoyloxy)-phenylacetamido]-3-(1-methyl-tetrazolyl-5-mercaptomethyl)-CC |
| 188. | 7-[2-D-amino-2-p-(3-ethoxycarbonyl-2-methyl-propanoyloxy)-phenylacetamido]-3-(1,3,4-thiadiazolyl-2-mercaptomethyl)-CC |
| 189. | 7-[2-D-amino-2-p-(3-ethoxycarbonyl-2-methyl-propanoyloxy)-phenylacetamido]-3-(2-methyl-1,3,4-thiadiazolyl-5-mercaptomethyl)-CC |
| 190. | 7-[2-D-amino-2-p-(2-ethoxycarbonyl-2-ethyl-acetoxy)-phenylacetamido]-CA |
| 191. | 7-[2-D-amino-2-p-(2-ethoxycarbonyl-2-ethyl-acetoxy)-phenylacetamido]-MCC |
| 192. | 7-[2-D-amino-2-p-(2-ethoxycarbonyl-2-ethyl-acetoxy)-phenylacetamido]-3-(1,2,3-triazolyl-5-mercaptomethyl)-CC |
| 193. | 7-[2-D-amino-2-p-(2-ethoxycarbonyl-2-ethyl-acetoxy)-phenylacetamido]-3-(1-methyltetrazolyl-5-mercaptomethyl)-CC |
| 194. | 7-[2-D-amino-2-p-(2-ethoxycarbonyl-2-ethyl-acetoxy)-phenylacetamido]-3-(1,3,4-thiadiazolyl-2-mercaptomethyl)-CC |
| 195. | 7-[2-D-amino-2-p-(2-ethoxycarbonyl-2-ethyl-acetoxy)-phenylacetamido]-3-(2-methyl-1,3,4-thiadiazolyl-5-mercaptomethyl)-CC |

EXAMPLE 196

As in Example 183, reaction of the triethylammonium salt of 6-(2-D-EMV-amino-2-p-hydroxyphenylacetamido)-PA with 2-ethoxycarbonyl-2-ethylethanoyl chloride and subsequent splitting off of the amino protective group during the work up produces 6-[2-D-amino-2-p-(4-ethoxycarbonyl-2-ethylacetoxy)-phenylacetamido]-PA.

EXAMPLE 197

To 5.78 g. of the triethylammonium salt of 6-(2-D-EMV-amino-2-p-hydroxyphenylacetamido)-PA, dissolved in 300 ml. of dichloromethane and 1.3 g. of triethylamine, are added dropwise, while cooling with ice, 2.3 g. of 2-ethoxycarbonyl-2-butylethanoyl chloride, dissolved in 40 ml. of dichloromethane. The reaction mixture is stirred for 30 minutes at 0°–5° C. Solvent is distilled off and the residue is worked up as described in Example 183 to give 6-[2-D-amino-2-p-(2-ethoxycarbonyl-2-butylacetoxy)-phenylacetamido]-PA.

As in Example 197, corresponding penicillanic and cephem derivatives of Formula (VII) react with monochlorides derived from compounds of Formula (IV)

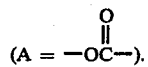

$(A = -OC-)$.

After removal of the amino protective group during the work up are obtained the corresponding compounds of Formula (I):

| Example | Compound of Formula (I) |
|---|---|
| 198. | 7-[2-D-amino-2-p-(2-methoxycarbonyl-2-methyl-acetoxy)-phenylacetamido]-CA |
| 199. | 7-[2-D-amino-2-p-(2-methoxycarbonyl-2-methyl-acetoxy)-phenylacetamido]-MCC |
| 200. | 7-[2-D-amino-2-p-(2-methoxycarbonyl-2-methyl-acetoxy)-phenylacetamido]-3-(1,2,3-triazolyl-5-mercaptomethyl)-CC |
| 201. | 7-[2-D-amino-2-p-(2-methoxycarbonyl-2-methyl-acetoxy)-phenylacetamido]-3-(1-methyltetrazolyl-5-mercaptomethyl)-CC |
| 202. | 7-[2-D-amino-2-p-(2-methoxycarbonyl-2-methyl-acetoxy)-phenylacetamido]-3-(1,3,4-thiadiazolyl-2-mercaptomethyl)-CC |
| 203. | 7-[2-D-amino-2-p-(2-methoxycarbonyl-2-methyl-acetoxy)-phenylacetamido]-3-(2-methyl-1,3,4-thiadiazolyl-5-mercaptomethyl)-CC |
| 204. | 6-[2-D-amino-2-p-(5-ethoxycarbonyl-2-methyl-pentanoyloxy)-phenylacetamido]-PA |
| 205. | 7-[2-D-amino-2-p-(5-ethoxycarbonyl-3-methyl-pentanoyloxy)-phenylacetamido]-CA |
| 206. | 7-[2-D-amino-2-p-(5-ethoxycarbonyl-4-methyl-pentanoyloxy)-phenylacetamido]-MCC |
| 207. | 7-[2-D-amino-2-p-(5-ethoxycarbonyl-5-methyl-pentanoyloxy)-phenylacetamido]-3-(1,2,3-triazolyl-5-mercaptomethyl)-CC |
| 208. | 7-[2-D-amino-2-p-(5-methoxycarbonyl-2-ethyl-pentanoyloxy)-phenylacetamido]-3-(1-methyl-tetrazolyl-5-mercaptomethyl)-CC |
| 209. | 7-[2-D-amino-2-p-(5-butyloxycarbonyl-2-propyl-pentanoyloxy)-phenylacetamido]-3-(1,3,4-thiadiazolyl-2-mercaptomethyl)-CC |
| 210. | 7-[2-D-amino-2-p-(5-hexyloxycarbonyl-3-propyl-pentanoyloxy)-phenylacetamido]-3-(2-methyl-1,3,4-thiadiazolyl-5-mercaptomethyl)-CC |
| 211. | 6-[2-D-amino-2-p-(6-methoxycarbonyl-2-methyl-hexanoyloxy)-phenylacetamido]-PA |
| 212. | 7-[2-D-amino-2-p-(6-methoxycarbonyl-2-ethyl-hexanoyloxy)-phenylacetamido]-CA |
| 213. | 6-[2-D-amino-2-p-(7-propyloxycarbonyl-2-methyl-heptanolyloxy)-phenylacetamido]-PA |
| 214. | 7-[2-D-amino-2-p-(7-propyloxycarbonyl-2-methyl-heptanoyloxy)-phenylacetamido]-CA |
| 215. | 6-[2-D-amino-2-p-(8-ethoxycarbonyl-2-methyl-actanoyloxy)-phenylacetamido]-PA |
| 216. | 7-[2-D-amino-2-p-(8-ethoxycarbonyl-2-methyl-octanoyloxy)-phenylacetamido]-CA |
| 217. | 6-[2-D-amino-2-p-(9-tert.-butyloxycarbonyl-nonanoyloxy)-phenylacetamido]-PA |
| 218. | 7-[2-D-amino-2-p-(9-tert.-butyloxycarbonyl-nonanoyloxy)-phenylacetamido]-CA |

EXAMPLE 219

The triethylammonium salt of 6-(2-D-EMV-amino-2-p-hydroxyphenylacetamido)-penicillanic acid (2.89 g.) is dissolved in 250 ml. of dichloromethane and 5.6 ml. of triethylamine and cooled with ice while 0.6 g. of 2-methoxyacetyl chloride, dissolved in 40 ml. of dichloromethane is added dropwise thereto. The reaction mixture is stirred and cooled with ice for 30 minutes. The solvent is distilled off. The oily residue is dissolved in 250 ml. of dilute aqueous sodium bicarbonate solution. The organic solvent is distilled off and the aqueous solution is extracted with ethyl acetate. The aqueous phase is adjusted to pH 3 with 1 N hydrochloric acid and extracted with 200 ml. of ethyl acetate. Solvent is distilled off to give, after chromatographic purification of the residue (silica gel/dioxane:water=85:15 v/v), 6-[2-D-amino-2-p-(2-methoxyacetoxy)-phenylacetamido]-PA.

As in Example 219, the triethylammonium salt of 6-[2-D-(EMV-amino)-2-p-hydroxyphenylacetamido]-PA, is reacted with appropriate acid chlorides of ω-hydroxy or ω-alkoxycarboxylic acids of Formula (IV) (A=—O—). Removal of the amino protective group during the isolation produces the following penicillanic acid derivatives of Formula (I):

| Example | Penicillanic Acid Derivative of Formula (I) |
|---|---|
| 200. | 6-[2-D-amino-2-p-(2-hydroxyacetoxy)-phenyl-acetamido]-PA |
| 221. | 6-[2-D-amino-2-p-(2-ethoxyacetoxy)-phenyl-acetamido]-PA |
| 222. | 6-[2-D-amino-2-p-(2-butyloxyacetoxy)-phenyl-acetamido]-PA |
| 223. | 6-[2-D-amino-2-p-(2-hexyloxyacetoxy)-phenyl-acetamido]-PA |
| 224. | 6-[2-D-amino-2-p-(3-ethoxypropanoyloxy)-phenyl-acetamido]-PA |
| 225. | 6-[2-D-amino-2-p-(4-hydroxybutanoyloxy)-phenyl-acetamido]-PA |
| 226. | 6-[2-D-amino-2-p-(4-ethoxybutanoyloxy)-phenyl-acetamido]-PA |
| 227. | 6-[2-D-amino-2-p-(6-propyloxypropanoyloxy)-phenyl-acetamido]-PA, $R_f$ = 0.39, IR: 1760 and 1692 cm.$^{-1}$ |
| 228. | 6-[2-D-amino-2-p-(8-ethoxyoctanoyloxy)-phenyl-acetamido]-PA |
| 228a. | 6-[-D-amino-2-p-(3-hexyloxypropanolyloxy)-phenyl-acetamido]-PA, $R_f$ = 0.46; IR: 1762 and 1685 cm.$^{-1}$ |

Analogously to Example 219, the triethylammonium salt of 7-[2-D-(EMV-amino)-2-p-hydroxyphenylacetamido]-CA reacts with appropriate acid chlorides of ω-hydroxy or ω-alkoxycarboxylic acids of Formula (IV). Subsequent work up results in splitting off of the amino protective group and produces the following cephalosporanic acids of Formula (I):

| Example | Cephalosporanic Acid of Formula (I) |
|---|---|
| 229. | 7-[2-D-amino-2-p-(2-hydroxyacetoxy)-phenyl-acetamido]-CA |
| 230. | 7-[2-D-amino-2-p-(2-methoxyacetoxy)-phenyl-acetamido]-CA |
| 231. | 7-[2-D-amino-2-p-(2-ethoxyacetoxy)-phenyl-acetamido]-CA |
| 232. | 7-[2-D-amino-2-p-(2-butyloxyacetoxy)-phenyl-acetamido]-CA |
| 233. | 7-[2-D-amino-2-p-(2-hexyloxyacetoxy)-phenyl-acetamido]-CA |
| 234. | 7-[2-D-amino-2-p-(3-ethoxypropanoyloxy)-phenyl-acetamido]-CA $[\alpha]_D^{20}$ = +36.5° (in ethanol) |
| 235. | 7-[2-D-amino-2-p-(4-hydroxybutanoyloxy)-phenyl-acetamido]-CA |
| 236. | 7-[2-D-amino-2-p-(4-ethoxybutanoyloxy)-phenyl-acetamido]-CA |
| 237. | 7-[2-D-amino-2-p-(6-ethoxyhexanoyloxy)-phenyl-acetamido]-CA |
| 238. | 7-[2-D-amino-2-p-(8-ethocyoxtanoyloxy)-phenyl-acetamido]-CA |

By the procedure of Example 219, the triethylammonium salt of 7-[2-D-(EMV-amino)-2-p-hydroxyphenylacetamido]-MCC is reacted with corresponding acid chlorides of ω-hydroxy or ω-alkoxycarboxylic acids of Formula (IV). The amino protective group following is removed during the work up, to produce the 3-methyl-3-cephem-4-carboxylic acid derivatives of Formula (I):

| Example | 3-Methyl-3-cephem-4-carboxylic Acid Derivatives of Formula (I) |
|---|---|
| 239. | 7-[2-D-amino-2-p-(2-hydroxyacetoxy)-phenyl-acetamido]-MCC |
| 240. | 7-[2-D-amino-2-p-(2-methoxyacetoxy)-phenyl-acetamido]-MCC |
| 241. | 7-[2-D-amino-2-p-(3-methoxypropanoyloxy)-phenyl-acetamido]-MCC, $R_f$ = 0.28 |
| 242. | 7-[2-D-amino-2-p-(4-hydroxybutanoyloxy)-phenyl-acetamido]-MCC |
| 243. | 7-[2-D-amino-2-p-(4-ethoxybutanoyloxy)-phenyl-acetamido]-MCC |

Analogously to Example 219, from the triethylammonium salt of 7-[2-D-(EMV-amino)-2-p-hydroxyphenylacetamido]-3-(1,2,3-triazolyl-5-mercaptomethyl)-CC, by reaction with corresponding acid chlorides of ω-hydroxy or ω-alkoxycarboxylic acids of Formula (IV) and subsequent splitting off of the amino protective group during the work up, are obtained the following 3-(1,2,3-triazolyl-5-mercaptomethyl)-3-cephem-4-carboxylic acid derivatives of Formula (I):

| Ex. | Compound of Formula (I) |
|---|---|
| 244. | 7-[2-D-amino-2-p-(2-hydroxyacetoxy)-phenyl-acetamido]-3-(1,2,3-triazolyl-5-mercaptomethyl)-CC |
| 245. | 7-[2-D-amino-2-p-(2-methoxyacetoxy)-phenyl-acetamido]-3-(1,2,3 triazolyl-5-mercaptomethyl)-CC |
| 246. | 7-[2-D-amino-2-p-(2-ethoxyacetoxy)-phenylacetamido]-3-(1,2,3-triazolyl-5-mercaptomethyl)-CC |
| 247. | 7-[2-D-amino-2-p-(2-butyloxyacetoxy)-phenylacetamido]-3-(1,2,3-triazolyl-5-mercaptomethyl)-CC |
| 248. | 7-[2-D-amino-2-p-(2-hexyloxyacetoxy)-phenyl-acetamido]-3-(1,2,3-triazolyl-5-mercaptomethyl)-CC |
| 249. | 7-[2-D-amino-2-p-(3-ethoxypropanoyloxy)-phenyl-acetamido]-3-(1,2,3-triazolyl-5-mercaptomethyl)-CC |
| 250. | 7-[2-D-amino-2-p-(4-hydroxybutanoyloxy)-phenyl-acetamido]-3-(1,2,3-triazolyl-5-mercaptomethyl)-CC |
| 251. | 7-[2-D-amino-2-p-(4-ethoxybutanoyloxy)-phenyl-acetamido]-3-(1,2,3-triazolyl-5-mercaptomethyl)-CC |
| 252. | 7-[2-D-amino-2-p-(6-ethoxyhexanoyloxy)-phenyl-acetamido]-3-(1,2,3-triazolyl-5-mercaptomethyl)-CC |
| 253. | 7-[2-D-amino-2-p-(8-ethoxyoctanoyloxy)-phenyl-acetamido]-3-(1,2,3-triazolyl-5-mercaptomethyl)-CC |

In accordance with the procedure of Example 219, the triethylammonium salt of 7-[2-D-(EMV-amino)-2-p-hydroxyphenylacetamido]-3-(1-methyltetrazolyl-5-mercaptomethyl)-CC is reacted with acid chlorides of ω-hydroxy- or ω-alkoxycarboxylic acids of Formula (IV) and subsequently worked up to give the following 3-(1-methyltetrazolyl-5-mercaptomethyl)-3-cephem-4-carboxylic acid derivatives of Formula (I):

| Ex. | Compound of Formula (I) |
|---|---|
| 254. | 7-[2-D-amino-p-(2-bydroxyacetoxy)-phenylacetamido]-3-[1-methyltetrazolyl-5-mercaptomethyl)-CC |
| 255. | 7-[2-D-amino-2-p-(2-methoxyacetoxy)-phenylacetamido]-3-[1-methyltetrazolyl-5-mercaptomethyl)-CC |
| 256. | 7-[2-D-amino-2-p-(2-ethoxyacetoxy)-phenylacetamido]-3-[1-methyltetrazolyl-5-mercaptomethyl)-CC |
| 257. | 7-[2-D-amino-2-p-(2-butyloxyacetoxy)-phenyl-acetamido]-3-(1-methyltetrazolyl-5-mercaptomethyl)-CC |
| 258. | 7-[2-D-amino-2-p-(2-hexyloxyacetoxy)-phenyl-acetamido]-3-(1-methyltetrazolyl-4-mercaptomethyl)-CC |
| 259. | 7-[2-D-amino-2-p-(3-ethoxypropanoyloxy)-phenyl-acetamido]-3-(1-methyltetrazolyl-5-mercaptomethyl)-CC, $R_f$ = 0.20 |

-continued

| Ex. | Compound of Formula (I) |
|---|---|
| 260. | 7-[2-D-amino-2-p-(4-hydroxybutanoyloxy)-phenylacetamido]-3-(1-methyltetrazolyl-5-mercaptomethyl)-CC |
| 261. | 7-[2-D-amino-2-p-(4-ethoxybutanoyloxy)-phenylacetamido]-3-(1-methyltetrazolyl-5-mercaptomethyl)-CC |
| 262. | 7-[2-D-amino-2-p-(6-ethoxyhexanoyloxy)-phenylacetamido]-3-(1-methyltetrazolyl-5-mercaptomethyl)-CC |
| 263. | 7-[2-D-amino-2-p-(8-ethoxyoctanoyloxy)-phenylacetamido]-3-(1-methyltetrazolyl-5-mercaptomethyl)-CC |

As in Example 219, the triethylammonium salt of 7-[2-D-(EMV-amino)-2-p-hydroxyphenylacetamido]-3-(1,3,4-thiadiazolyl-2-mercaptomethyl)-CC reacts with corresponding acid chlorides of ω-hydroxy- or ω-alkoxycarboxylic acids of Formula (IV). Subsequent splitting off of the amino protective group during the work up produces the following 3-(1,3,4-thiadiazolyl-2-mercaptomethyl)-3-cephem-4-carboxylic acid derivatives of Formula (I):

| Example | Compound of Formula (I) |
|---|---|
| 264. | 7-[2-D-amino-2-p-(2-hydroxyacetoxy)-phenylacetamido]-3-(1,3,4-thiadiazolyl-2-mercaptomethyl)-CC |
| 265. | 7-[2-D-amino-2-p-(2-methoxyacetoxy)-phenylacetamido]-3-(1,3,4-thiadiazolyl-2-mercaptomethyl)-CC |
| 266. | 7-[2-D-amino-2-p-(2-ethoxyacetoxy)-phenylacetamido]-3-(1,3,4-thiadiazolyl-2-mercaptomethyl)-CC |
| 267. | 7-[2-D-amino-2-p-(2-butyloxyacetoxy)-phenylacetamido]-3-(1,3,4-thiadiazolyl-2-mercaptomethyl)-CC |
| 268. | 7-[2-D-amino-2-p-(2-hexyloxyacetoxy)-phenylacetamido]-3-(1,3,4-thiadiazolyl-2-mercaptomethyl)-CC |
| 269. | 7-[2-D-amino-2-p-(3-ethoxypropanoyloxy)-phenylacetamido]-3-(1,3,4-thiadiazolyl-2-mercaptomethyl)-CC |
| 270. | 7-[2-D-amino-2-p-(4-hydroxybutanoyloxy)-phenylacetamido]-3-(1,3,4-thiadiazolyl-2-mercaptomethyl)-CC |
| 271. | 7-[2-D-amino-2-p-(4-ethoxybutanoyloxy)-phenylacetamido]-3-(1,3,4-thiadiazolyl-2-mercaptomethyl)-CC |
| 272. | 7-[2-D-amino-2-p-(6-ethoxyhexanoyloxy)-phenylacetamido]-3-(1,3,4-thiadiazolyl-2-mercaptomethyl)-CC |
| 273. | 7-[2-D-amino-2-p-(8-ethoxyoctanoyloxy)-phenylacetamido]-3-(1,3,4-thiadiazolyl-2-mercaptomethyl)-CC |

By the method of Example 219, the triethylammonium salt of 7-[2-D-(EMV-amino)-2-p-hydroxyphenyl-acetamido]-3-(2-methyl-1,3,4-thiadiazolyl-5-mercaptomethyl)-CC reacts with appropriate acid chlorides of ω-hydroxy- or ω-alkoxycarboxylic acids of Formula (IV) and is worked up with splitting off of the amino protective group to give the following 3-(2-methyl-1,3,4-thiadiazolyl-5-mercaptomethyl)-3-cephem-4-carboxylic acid derivatives of Formula (I):

| Example | Compound of Formula (I) |
|---|---|
| 274. | 7-[2-D-amino-2-p-(2-hydroxyacetoxy)-phenylacetamido]-3-(2-methyl-1,3,4-thiadiazolyl-5-mercaptomethyl)-CC |
| 275. | 7-[2-D-amino-2-p-(2-methoxyacetoxy)-phenylacetamido]-3-(2-methyl-1,3,4-thiadiazolyl-5-mercaptomethyl)-CC |
| 276. | 7-[2-D-amino-2-p-(2-ethoxyacetoxy)-phenylacetamido]-3-(2-methyl-1,3,4-thiadiazolyl-5-mercaptomethyl)-CC |

-continued

| Example | Compound of Formula (I) |
|---|---|
| 277. | 7-[2-D-amino-2-p-(2-butyloxyacetoxy)-phenylacetamido]-3-(2-methyl-1,3,4-thiadiazolyl-5-mercaptomethyl)-CC |
| 278. | 7-[2-D-amino-2-p-(2-hexyloxyacetoxy)-phenylacetamido]-3-(2-methyl-1,3,4-thiadiazolyl-5-mercaptomethyl)-CC |
| 279. | 7-[2-D-amino-2-p-(3-ethoxypropanoyloxy)-phenylacetamido]-3-(2-methyl-1,3,4-thiadiazolyl-5-mercaptomethyl)-CC |
| 280. | 7-[2-D-amino-2-p-(4-hydroxybutanoyloxy)-phenylacetamido]-3-(2-methyl-1,3,4-thiadiazolyl-5-mercaptomethyl)-CC |
| 281. | 7-[2-D-amino-2-p-(4-ethoxybutanoyloxy)-phenylacetamido]-3-(2-methyl-1,3,4-thiadiazolyl-5-mercaptomethyl)-CC |
| 282. | 7-[2-D-amino-2-p-(6-ethoxyhexanoyloxy)-phenylacetamido]-3-(2-methyl-1,3,4-thiadiazolyl-5-mercaptomethyl)-CC |
| 283. | 7-[2-D-amino-2-p-(8-ethoxyoctanoyloxy)-phenylacetamido]-3-(2-methyl-1,3,4-thiadiazolyl-5-mercaptomethyl)-CC |

EXAMPLE 284

(a) A mixture of 3.28 g. of 3-desacetoxy-7-aminocephalosporanic acid tert.-butyl ester (7-amino-MCC-tert.-butyl ester), 3.51 g. of 2-formylamino-2-p-(4-hydroxybutanoyloxy)-phenylacetic acid, obtained from 2-formylamino-2-p-hydroxyphenylacetic acid and γ-butyrolactone in the presence of triethylamine, 2.5 g. of DCC, 20 ml. of dry DMF and 10 ml. of dry dichloromethane are stirred for 2 hours at ambient temperature and filtered. About half the solvent is distilled off. The residue is put on a silica gel column and eluted with ethyl acetate. From the eluate is obtained, after removal of solvent, 7-[2-formylamino-2-p-(4-hydroxybutanoyloxy)-phenylacetamido]-MCC tert.-butyl ester as residue.

(b) 7-[2-Formylamino-2-p-(4-hydroxybutanoyloxy)-phenylacetamido]-MCC tert.-butyl ester (1.8 g.) is dissolved in 15 ml. of dry trifluoroacetic acid and stirred for 15 minutes at ambient temperature. The trifluoroacetic acid is distilled off to give a residue of 7-[2-formylamino-2-p-(4-hydroxybutanoyloxy)-phenylacetamido]-MCC.

(c) A mixture of 0.6 g. of 7-[2-formylamino-2-p-(4-hydroxybutanoyloxy)-phenylacetamido]-MCC tert.-butyl ester, 30 ml. of THF and 4 ml. of concentrated aqueous hydrochloric acid is allowed to stand overnight at 5° and than poured into water and extracted with ethyl acetate to give, after removal of the solvent, 7-[2-amino-2-p-(4-hydroxybutanoyloxy)-phenylacetamido]-MCC tert.-butyl ester as residue.

(d) 7-[2-Amino-2-p-(4-hydroxybutanoyloxy)-phenylacetamido]-MCC tert.-butyl ester (0.4 g.) is dissolved in 10 ml. of trifluoroacetic acid and stirred for 30 minutes at 5° C. The solvent is distilled off to give a residue of the trifluoroacetate of 7-[2-amino-2-p-(4-hydroxybytanoyloxy)-phenylacetamido]-MCC. This salt is dissolved in 25 ml. of water and stirred for 1 hour at 25° C. with 15 g. of a polystyrene-amine ion exchange resin ("Amberlite" IR-45). The ion exchange resin is separated off and the aqueous solution is lyophilized to give 7-[2-amino-2-p-(4-hydroxybutanoyloxy)-phenylacetamido]-MCC (betaine form).

EXAMPLE 285

7-[2-BOC-amino-2-p-(2-hydroxyacetoxy)-phenylacetamido]-CA (2.8 g.) is stirred for 30 minutes at 20° C. in a mixture of 10 ml. of trifluoroacetic acid and 5 ml. of anisole and solvent is distilled off to give 7-[2-amino-2-p-(2-hydroxyacetoxy)-phenylacetamido]-CA as the trifluoroacetate. The free acid can be obtained therefrom, as described in Example 284(d), in betaine form.

The starting material is obtained by reaction of 2-BOC amino-2-p-(2-hydroxyacetoxy)-phenylacetic acid, obtained from 2-amino-2-p-(2-hydroxyacetoxy)-phenylacetic acid and tert.-butoxycarbonyl azide in the presence of magnesium oxide, with 7-ACA in the presence of ethyl chloroformate.

EXAMPLE 286

6-APA triethylamine salt (3.17 g.) dissolved in 40 ml. of dichloromethane is added dropwise at −10° C. to a solution of ethyl-2-D-(2-ethoxycarbonyl-1-methylvinylamino)-2-p-ethoxycarbonyloxyphenylethanoyl carbonate, prepared in situ from 2.79 g. of 2-D-(2-ethoxycarbonyl-1-methylvinylamino)-2-p-hydroxyphenylacetic acid and 2.17 g. of ethyl chloroformate in the presence of 7 ml. of triethylamine, in 100 ml. of dichloromethane. The reaction mixture is allowed to come slowly to ambient temperature and extracted with 80 ml. of water. The aqueous phase ia adjusted to pH 3 with 1 N aqueous hydrochloric acid, extracted with ethyl acetate and allowed to stand overnight. Precipitation with petroleum ether gives 6-(2-D-amino-p-ethoxycarbonyloxyphenylacetamido)-PA; $R_f$=0.41 (silica gel/dioxane:water=85:15 v/v).

EXAMPLE 287

(a) 7-[2-Formylamino-2-p-(4-hydroxybutanoyloxy)-phenylacetamido]-CA (1.5 g.), obtained analogously to Example 284(a) and (b) from 7-ACA-tert.-butyl ester and 2-formylamino-2-p-(4-hydroxybutanoyloxy)-phenylacetic acid and subsequent treatment of the reaction product with trifluoroacetic acid, and 230 mg. of 1-methyl-tetrazolyl-5-thiol are suspended in 8 ml. of water at ambient temperature. The reactants are brought into solution by the addition of sodium bicarbonate. The resulting pH is between 4 and 7. The reaction mixture is heated for 30 minutes at 70° C. and, after cooling, adjusted to pH 2 with concentrated hydrochloric acid and filtered. After chromatographic purification of the residue (silica gel/dioxane:water=85:15 v/v), is obtained 7-[2-formylamino-2-p-(4-hydroxybutanoyloxy)-phenylacetamido]-3-(1-methyltetrazolyl-5-mercaptomethyl)-CC.

(b) As in Example 284(c), from 7-[2-formylamino-2-p-(4-hydroxybutanoyloxy)-phenylacetamido]-3-(1-methyltetrazolyl-5-mercaptomethyl)-CC, by reaction with hydrochloric acid, is obtained 7-[2-amino-2-p-(4-hydroxybutanoyloxy)-phenylacetamido]-3-(1-methyltetrazolyl-5-mercaptomethyl)-CC.

EXAMPLE 288

The triethylammonium salt of 7-(2-D-BOC-amino-2-p-hydroxyphenylacetamido)-CA, (6.22 g.) is dissolved in 250 ml. of dichloromethane and 10 ml. of triethylamine and cooled with ice while 1.7 g. of succinic acid monomethyl ester monochloride, dissolved in 40 ml. of dichloromethane, is added dropwise thereto. The reaction mixture is stirred for 40 minutes at 0°–5° C. and the solvent is removed by distillation. The residue is stirred for 30 minutes with trifluoroacetic acid and the trifluoroacetic acid is distilled off. The residue is dissolved in 80 ml. of THF and the filtrate is added to 350 ml. of dilute aqueous sodium bicarbonate solution. The organic solvent is distilled off and the aqueous solution is extracted with ethyl acetate. The pH of the aqueous phase is adjusted to 3 with hydrochloric acid and the aqueous phase is extracted with ethyl acetate. After distilling off solvent, there is obtained 7-[2-D-amino-2-p-(3-methoxycarbonylpropanoyloxy)-phenylacetamido]-CA; $R_f$=0.58 (silica gel/dioxane:water=9:1 v/v); $[\alpha]_D^{20}$= +61.2° (in ethanol).

EXAMPLE 289

As in Example 288, from the triethylammonium salt of 7-(2-D-BOC-amino-p-hydroxyphenylacetamido)-CA, by reaction with 3-methoxypropionyl chloride and removal of the BOC group with trifluoroacetic acid, is obtained 7-[2-D-amino-2-p-(3-methoxypropionyloxy)-phenylacetamido]-CA; $R_f$=0.28 (silica gel/dioxane:water=9:1 v/v); $[\alpha]_D^{20}$= +59.8° (in ethanol).

EXAMPLE 290

7-ACA (2.7 g.) is suspended in 50 ml. of dry acetonitrile. Triethylamine (1 g.) and 2 ml. of N,N-dimethylaniline are added thereto and the mixture is cooled to 5° C. Trimethylchorosilane (12.7 g.) is added dropwise thereto. After 10 minutes, 3.3 g. of 2-D-amino-2-p-(3-ethoxypropionyloxy)-phenylacetyl chloride hydrochloride, obtained from a suspension of 2-D-amino-2-p-(3-ethoxypropionyloxy)-phenylacetic acid in dry dioxane by successive introduction of dry phosgene and dry gaseous hydrogen chloride, dissolved in 80 ml. of dry dioxane, are added dropwise. The reaction mixture is stirred for 1 hour at 10° C., after which 40 ml. of water are added dropwise. The pH is adjusted to 2.5 with solid sodium carbonate and the organic phase is separated off. The pH is of the aqueous phase is adjusted to 2 with hydrochloric acid and the aqueous phase is washed with diethyl ether. The aqueous phase is adjusted with dilute aqueous sodium hydroxide solution to pH 4, and concentrated to an appearance of turbidity. The turbid solution is allowed to stand overnight at 5° C., and filtered. The recovered precipitate is dried to give 7-[2-D-amino-2-p-(3-ethoxypropionyloxy)-phenylacetamido]-CA; $R_f$=0.29 (silica gel/dioxane:water=9:1 v/v); $[\alpha]_D^{20}$= +36.5° (in ethanol).

The compounds Formula (I) mentioned in Examples 1 to 289 are obtained analogously by the reaction of trimethylsilyl esters of compounds of Formula (II), prepared in situ, with corresponding acid chloride hydrochlorides of Formula (III).

EXAMPLE 291

7-[2-D-Amino-2-p-(5-methoxycarbonylpentanoyloxy)-phenylacetamido]-CA (563 mg.) and 84 mg. of sodium bicarbonate are dissolved in 13 ml. of water and stirred for 30 minutes at ambient temperature to give, after freeze drying the solution, the sodium salt of 7-[2-D-amino-2-p-(5-methoxycarbonylpentanoyloxy)-phenylacetamido]-CA.

As in Example 288, reaction of 2-acetoxyacetyl chloride with corresponding BOC derivatives of Formula (VII) and subsequent splitting off of the amino protective group during the work up, produces the following compounds of Formula (I):

| | |
|---|---|
| 292. | 6-[2-D-amino-2-p-(2-acetoxyacetoxy)-phenyl-acetamido]-PA |
| 293. | 7-[2-D-amino-2-p-(acetoxyacetoxy)-phenyl-acetamido]-CA |
| 294. | 7-[2-D-amino-2-p-(2-acetoxyacetoxy)-phenyl-acetamido)-MCC |
| 295. | 7-[2-D-amino-2-p-(2-acetoxyacetoxy)-phenyl-acetamido]-3-(1,2,3-thiazolyl-5-mercapto-methyl)-CC |
| 296. | 7-[2-D-amino-2-p-(2-acetoxyacetoxy)-phenyl-acetamido]-3-(1-methyltetrazolyl-5-mercapto-methyl)-CC |
| 297. | 7-[2-D-amino-2-p-(2-acetoxyacetoxy)-phenyl-acetamido]-3-(1,3,4-thiadiazolyl-2-mercapto-methyl)-CC |
| 298. | 7-[2-D-amino-2-p-(2-acetoxyacetoxy)-phenyl-acetamido]-3-(2-methyl-1,3,4-thiadiazolyl-5-mercaptomethyl)-CC |

In accordance with Example 288, 2-acetoxypropanoyl chloride is reacted with corresponding BOC derivatives of Formula (VII). Subsequent removal during the work up of the amino protective group produces the corresponding compounds of Formula (I):

| Ex. | Compound of Formula (I) |
|---|---|
| 299. | 6-[2-D-amino-p-(2-acetoxypropanoyloxy)-phenyl-acetamido]-PA |
| 300. | 7-[2-D-amino-2-p-(2-acetoxypropanoyloxy)-phenyl-acetamido]-CA |
| 301. | 7-[2-D-amino-2-p-(2-acetoxypropanoyloxy)-phenyl-acetamido]-MCC |
| 302. | 7-[2-D-amino-2-p-(2-acetoxypropanoyloxy)-phenyl-acetamido]-3-(1,2,3-thiazolyl-5-mercaptomethyl)-CC |
| 303. | 7-[2-D-amino-2-p-(2-acetoxypropanoyloxy)-phenyl-acetamido]-3-(1-methyltetrazolyl-4-mercaptomethyl)-CC |
| 304. | 7-[2-D-amino-2-p-(2-acetoxypropanoyloxy)-phenyl-acetamido]-3-(1,3,4-thiadiazolyl-2-mercaptomethyl)-CC |
| 305. | 7-[2-D-amino-2-p-(2-acetoxypropanoyloxy)-phenyl-acetamido]-3-(2-methyl-1,3,4-thiadiazolyl-5-mercaptomethyl)-CC |

As in Example 219, the triethylammonium salt of 7-[2-D-(EMV-amino)-2-p-hydroxyacetamido]-MCC, by reaction with corresponding acid chlorides of ω-alkoxycarboxylic acids of Formula (IV) and subsequent cleavage during work up of the amino protective group, gives the following 3-methyl-3-cephem-4-carboxylic acid derivatives of Formula (I):

| Example | 3-Methyl-3-cephem-4-carboxylic Acid Derivative of Formula (I) |
|---|---|
| 306. | 7-[2-D-amino-2-p-(3-methoxypropanoyloxy)-phenyl-acetamido]-MCC |
| 307. | 7-[2-D-amino-2-p-(3-ethoxypropanoyloxy)-phenyl-acetamido]-MCC |
| 308. | 7-[2-D-amino-2-p-(2-propyloxyacetoxy)-phenyl-acetamido]-MCC |
| 309. | 7-[2-D-amino-2-p-(3-propyloxypropanoyloxy)-phenyl-acetamido]-MCC |

From carboxylic acids of Formula (I) mentioned in the preceding Examples, sodium salts are obtained analogously by reaction with sodium bicarbonate.

Active materials of Formula (I), especially those mentioned in the preceding Examples and readily-cleavable esters and physiologically-acceptable salts thereof can be formulated in the usual manner, together with adjuvant and/or carrier materials conventional in pharmacy, to give pharmaceutical compositions. This illustrated by the following Examples:

EXAMPLE A

Ampoules

A solution of 100 g. of 7-[2-D-amino-2-p-(5-methoxycarbonylpentanoyloxy)-phenylacetamido]-cephalosporanic acid sodium salt in 0.3 liters of twice distilled water is sterilized by filtration, filled into ampoules, lyophilized under sterile conditions and sealed in a sterile manner. Each ampoule contains 1 g. of active material.

Ampoules containing a solvent are obtained by dissolving 50 g. of 6-(2-D-amino-p-ethoxycarbonyloxy-phenylacetamido)-penicillanic acid in 3 liters of twice distilled water and, after sterilization by filtration, charged into ampoules which are sterilized for 20 minutes at 120° C. Each ampoule contains 50 g. of in 3 ml. of water.

EXAMPLE B

Tablets

A mixture of 100 g. of 7-[2-D-amino-2-p-(5-methoxycarbonylpentanoyloxy)-phenylacetamido]-penicillanic acid sodium salt, 500 g. of lactose, 180 g. of wheat starch, 10 g. of cellulose powder and 10 g. of magnesium stearate is pressed, in the usual way, into tablets in such a manner that each tablet contains 50 mg. of active material.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

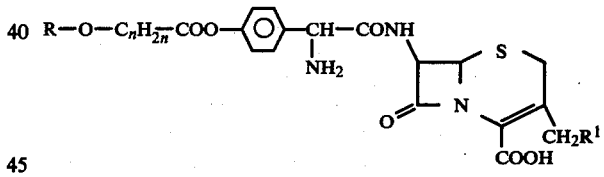

wherein R is alkyl of up to 6 carbon atoms or H; R¹ is hydrogen or acetoxy; and n is 0 or an integer from 1 to 8; or a readily-cleavable ester or a pharmaceutically acceptable salt of the carboxy group thereof; said readily-cleavable ester being a tert-butyl, trimethylsilyl, benzyl, benzhydryl, trichloroethyl, benzylmethyl, p-methoxybenzyl, methoxymethyl or pivaloyloxymethyl ester.

2. 7-[2-D-Amino-2-p-(3-ethoxypropionyloxy)-phenylacetamido]-cephalosporanic acid, a compound of claim 1.

3. 7-[2-D-amino-2-p-(3-propyloxypropanoyloxy)-phenylacetamido]-3-methyl-3-cephem-4-carboxylic acid, a compound of claim 1.

4. A pharmaceutical compositions, comprising an amount per unit dosage effective to produce a systemic antibacterial effect upon administration, of a compound of claim 1, in admixture with a pharmaceutically-acceptable carrier.

5. A method of treating a patient afflicted with a bacterial infection comprising administering to the affected patient an antibacterial amount of a compound of claim 1.